US012603150B2

(12) United States Patent
Barber

(10) Patent No.: US 12,603,150 B2
(45) Date of Patent: Apr. 14, 2026

(54) CALCULATING CELL-TYPE RNA PROFILES FOR DIAGNOSIS AND TREATMENT

(71) Applicant: Tempus AI, Inc., Chicago, IL (US)

(72) Inventor: Mathew Barber, Chicago, IL (US)

(73) Assignee: Tempus AI, Inc., Chicago, IL (US)

( * ) Notice: Subject to any disclaimer, the term of this patent is extended or adjusted under 35 U.S.C. 154(b) by 1370 days.

(21) Appl. No.: 17/074,984

(22) Filed: Oct. 20, 2020

(65) Prior Publication Data

US 2021/0118526 A1 Apr. 22, 2021

Related U.S. Application Data

(60) Provisional application No. 62/924,054, filed on Oct. 21, 2019.

(51) Int. Cl.
*G16B 25/10* (2019.01)
*G16B 40/20* (2019.01)
*G16B 40/30* (2019.01)

(52) U.S. Cl.
CPC ............. *G16B 25/10* (2019.02); *G16B 40/20* (2019.02); *G16B 40/30* (2019.02)

(58) Field of Classification Search
CPC ......... G16B 25/10; G16B 40/20; G16B 40/30
See application file for complete search history.

(56) References Cited

U.S. PATENT DOCUMENTS

2012/0301887 A1 11/2012 Bankaitis-Davis et al.
2019/0119730 A1 4/2019 Spurlock

OTHER PUBLICATIONS

Tsoucas, D., Dong, R., Chen, H. et al. Accurate estimation of cell-type composition from gene expression data. Nat Commun 10, 2975 (2019). 9 pages. https://doi.org/10.1038/s41467-019-10802-z (Year: 2019).*
Sun X, Sun S, Yang S. An Efficient and Flexible Method for Deconvoluting Bulk RNA-Seq Data with Single-Cell RNA-Seq Data. Cells. 2019; 8(10):1161. https://doi.org/10.3390/cells8101161 (Year: 2019).*
Liron Pantanowitz, Paul N. Valenstein, Andrew J. Evans, Keith J. Kaplan, John D. Pfeifer, David C. Wilbur, Laura C. Collins, Terence J. Colgan, Review of the current state of whole slide imaging in pathology, Journal of Pathology Informatics, vol. 2, Issue 1, 2011 (Year: 2011).*
Gong, Ting, et al. "DeconRNASeq: a statistical framework for deconvolution of heterogeneous tissue samples based on mRNA-Seq data", Bioinformatics, vol. 29, No. 8, 2013, pp. 1083-1085.
Newman, Aaron M., et al. "Robust enumeration of cell subsets from tissue expression profiles", Nature Methods, vol. 12, No. 5, May 2015, pp. 453-462.

(Continued)

*Primary Examiner* — Larry D Riggs, II
*Assistant Examiner* — Emilie A Smith
(74) *Attorney, Agent, or Firm* — MORGAN, LEWIS & BOCKIUS LLP

(57) ABSTRACT

Methods for determining a cancer composition of a subject are provided that include generating machine-learning models configured to identify cell types based on respective cell-type RNA expression profiles, and using the models to determine the cancer composition of the subject.

26 Claims, 17 Drawing Sheets
(7 of 17 Drawing Sheet(s) Filed in Color)

(56) References Cited

OTHER PUBLICATIONS

Newman, Aaron M., et al. "Determining cell type abundance and expression from bulk tissues with digital cytometry", Nature Biotechnology, Dec. 15, 2017, pp. 1-16.

Newman, Aaron M., et al. Supplementary Information: "Determining cell type abundance and expression from bulk tissues with digital cytometry", Dec. 15, 2017, Nature Biotechnology, pp. 1-43.

* cited by examiner

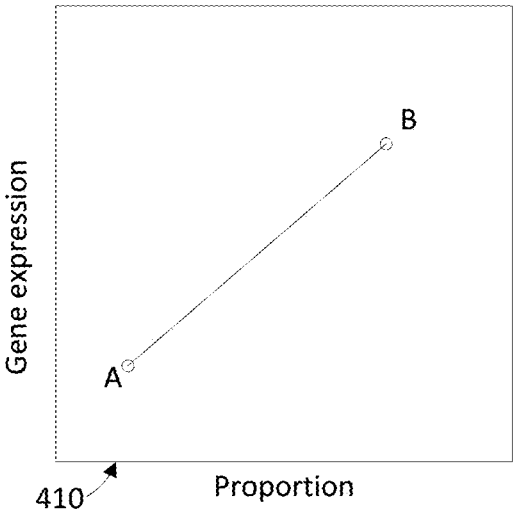
410
Proportion
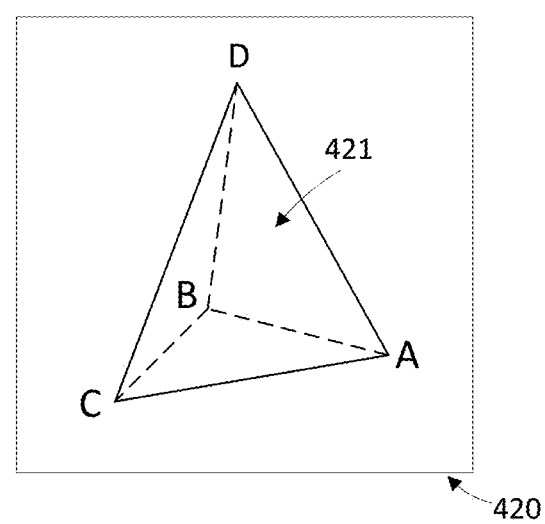
421
420
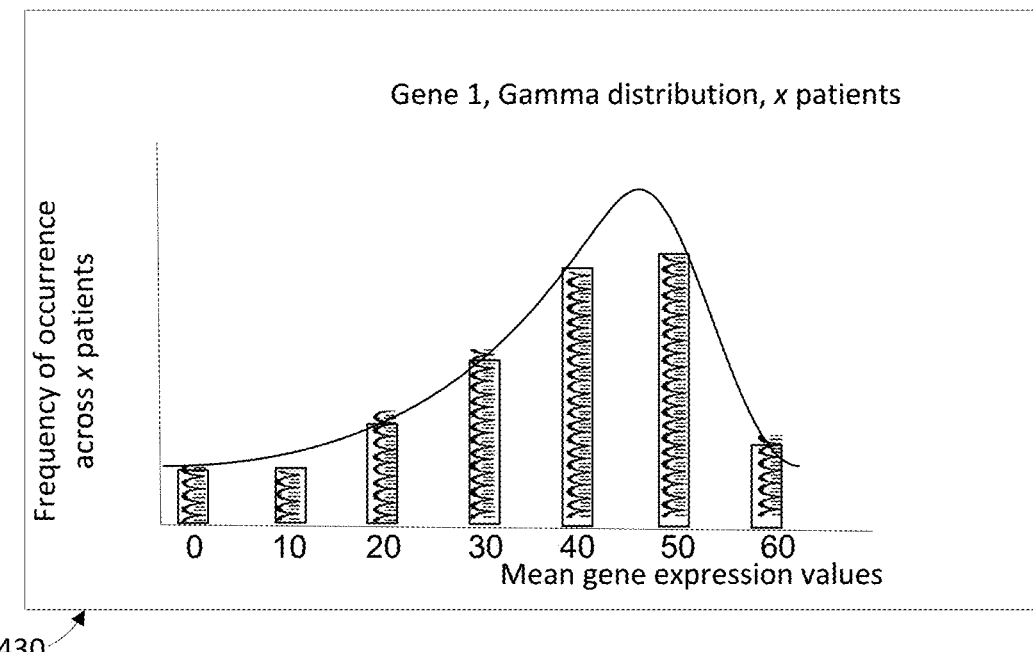
Gene 1, Gamma distribution, x patients
430
FIG. 4

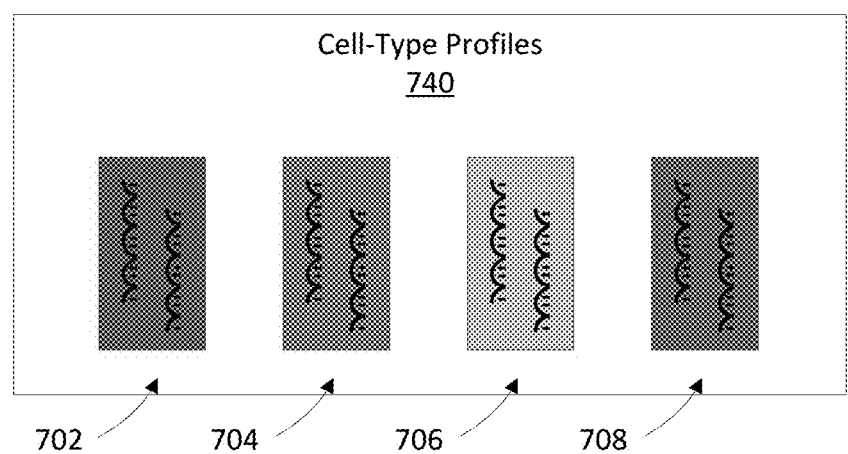
Cell-Type Profiles
740
702  704  706  708
750
Slide Profile: $\sum$ Tumor + Lymphocytes + Stroma + Epithelium
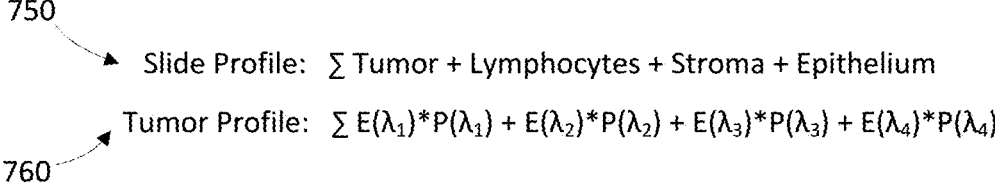
Tumor Profile: $\sum E(\lambda_1)*P(\lambda_1) + E(\lambda_2)*P(\lambda_2) + E(\lambda_3)*P(\lambda_3) + E(\lambda_4)*P(\lambda_4)$
760
|  | Gene 1 | Gene 2 | Gene 3 | Gene 4 | Gene ... | Gene N |
|---|---|---|---|---|---|---|
| Tumor 722 |  |  |  |  |  |  |
| $\lambda_1$ 724 | 100 | 0 | 0 | 850 | ... | 0 |
| $\lambda_2$ 726 | 120 | 0 | 100 | 650 | ... | 0 |
| $\lambda_3$ 728 | 80 | 30 | 50 | 0 | ... | 50 |
| $\lambda_4$ 730 | 350 | 0 | 200 | 700 | ... | 100 |
| Lymphocytes 734 | 0 | 550 | 380 | 380 | ... | 0 |
| Stroma 736 | 850 | 100 | 0 | 550 | ... | 975 |
| Epithelium 738 | 620 | 0 | 380 | 100 | ... | 550 |
770
FIG. 7

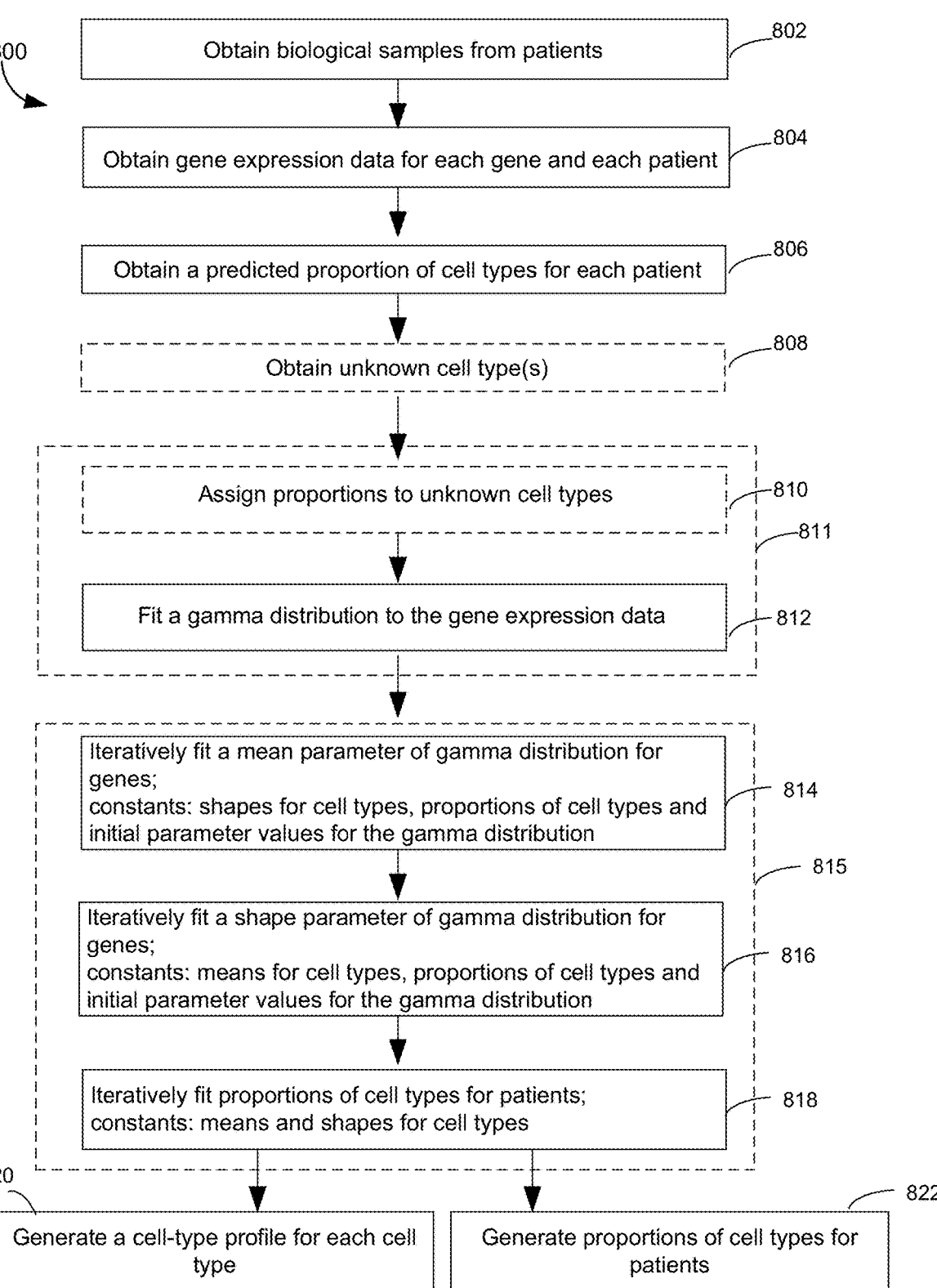

800

| | |
|---|---|
| Obtain biological samples from patients | 802 |

| | |
|---|---|
| Obtain gene expression data for each gene and each patient | 804 |

| | |
|---|---|
| Obtain a predicted proportion of cell types for each patient | 806 |

| | |
|---|---|
| Obtain unknown cell type(s) | 808 |

| | |
|---|---|
| Assign proportions to unknown cell types | 810 |

811

| | |
|---|---|
| Fit a gamma distribution to the gene expression data | 812 |

| | |
|---|---|
| Iteratively fit a mean parameter of gamma distribution for genes; constants: shapes for cell types, proportions of cell types and initial parameter values for the gamma distribution | 814 |

815

| | |
|---|---|
| Iteratively fit a shape parameter of gamma distribution for genes; constants: means for cell types, proportions of cell types and initial parameter values for the gamma distribution | 816 |

| | |
|---|---|
| Iteratively fit proportions of cell types for patients; constants: means and shapes for cell types | 818 |

820

| | |
|---|---|
| Generate a cell-type profile for each cell type | Generate proportions of cell types for patients |

A method for determining a cancer composition of a subject is provided.

⌐— 1004

Generate, in electronic form, for each respective genetic target in a first plurality of genetic targets, a corresponding shape parameter, based at least in part on RNA sequencing of one or more respective biological samples obtained from a respective tumor specimen of each respective subject across a plurality of subjects.

1006

The first plurality of genetic targets are a first plurality of genes.

1008

The first plurality of genetic targets is a transcriptome.

1010

Each genetic target is a different independent RNA for a corresponding gene in a plurality of genes.

1012

The first plurality of genetic targets is a first plurality of genetic loci.

1014

The one or more respective biological samples are one or more pathology tissue slides.

⌐— 1016

Obtain, in electronic form, for each respective subject across the plurality of subjects, a corresponding relative proportion of one or more sets of cell types in a plurality of sets of cell types.

1018

The relative proportion of one or more sets of cell types in the plurality of sets of cell types is obtained by initializing the relative proportion of one or more sets of cell types in the plurality of sets of cell types to random proportions.

1020

The relative proportion of one or more sets of cell types in the plurality of sets of cell types provides proportions is obtained for less than the entirety of the plurality of sets of cell types.

1022

The relative proportion of the one or more sets of cell types in the plurality of sets of cell types for a corresponding subject originates from a pathology report for the corresponding subject.

FIG. 10A

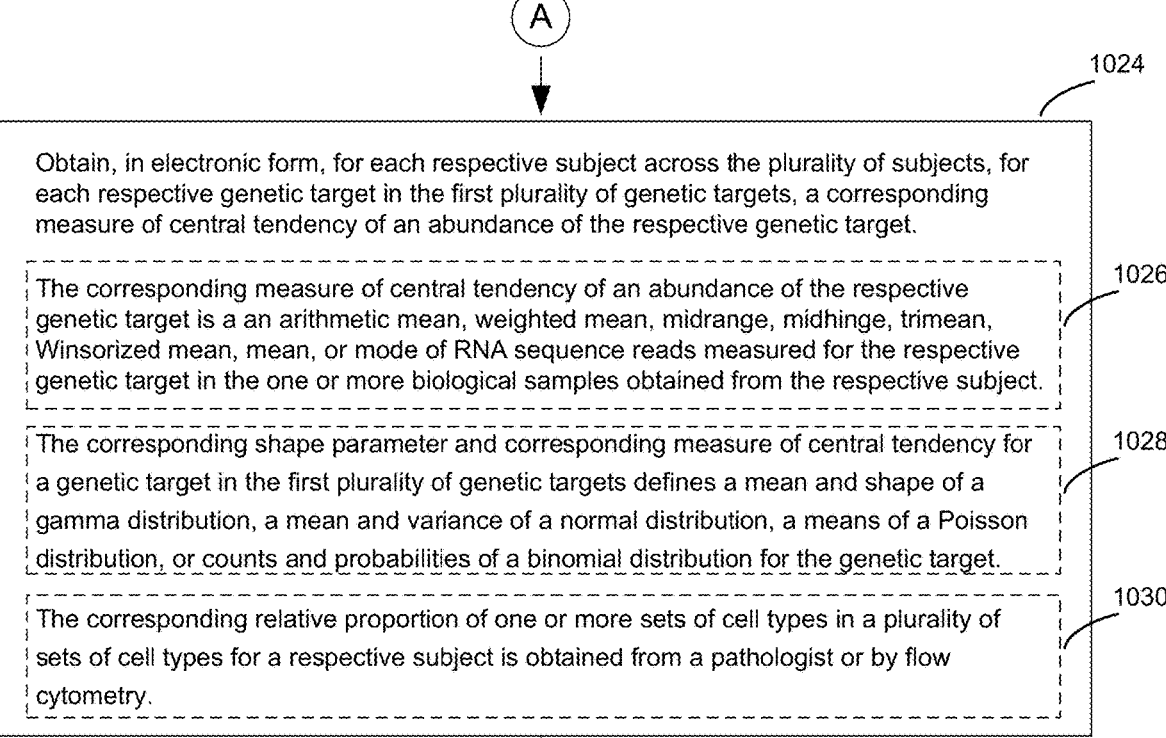

Ⓐ

1024

Obtain, in electronic form, for each respective subject across the plurality of subjects, for each respective genetic target in the first plurality of genetic targets, a corresponding measure of central tendency of an abundance of the respective genetic target.

1026

The corresponding measure of central tendency of an abundance of the respective genetic target is a an arithmetic mean, weighted mean, midrange, midhinge, trimean, Winsorized mean, mean, or mode of RNA sequence reads measured for the respective genetic target in the one or more biological samples obtained from the respective subject.

1028

The corresponding shape parameter and corresponding measure of central tendency for a genetic target in the first plurality of genetic targets defines a mean and shape of a gamma distribution, a mean and variance of a normal distribution, a means of a Poisson distribution, or counts and probabilities of a binomial distribution for the genetic target.

1030

The corresponding relative proportion of one or more sets of cell types in a plurality of sets of cell types for a respective subject is obtained from a pathologist or by flow cytometry.

1032

Refine the first optimization model subject to a first plurality of constraints.

The first plurality of constraints include: (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects, the refining thereby identifying a plurality of calculated cell types in a first set of cell types in the plurality of sets of cell types, the refining further generating a respective calculated cell type RNA expression profile for each calculated cell type in the plurality of calculated cell types.

1034

Use the respective calculated cell type RNA expression profile for each calculated cell type in the plurality of calculated cell types to determine a cancer composition of a subject.

1036

The using comprises: obtaining, in electronic form, a test expression set that comprises, for each respective genetic target in the first plurality of genetic targets, a corresponding measure of central tendency of an abundance of the respective genetic target, at least in part on RNA sequencing of one or more respective biological samples obtained from a tumor specimen of a test subject; obtaining, in electronic form, a test proportion set that comprises the corresponding relative proportion of each set of cell types in the plurality of sets of cell types; and refining a second optimization model subject to a second plurality of constraints. The second plurality of constraints include (i) the test expression set, (ii) the test proportion set, and (iii) the respective calculated cell type RNA expression profile for each calculated cell type in the plurality of calculated cell types, thereby identifying the cancer composition of the test subject in the form of a relative proportion of each calculated cell type in the plurality of calculated cells types.

FIG. 10C

| | | | | | | | | | | |
|---|---|---|---|---|---|---|---|---|---|---|
| ABCB1 | ABCC3 | ABL1 | ABL2 | ACTA2 | ACVR1B | AJUBA | AKT1 | AKT2 | AKT3 | ALK |
| AMER1 | APC | APOB | AR | ARAF | ARHGAP26 | ARHGAP35 | ARID1A | ARID1B | ARID2 | ARID5B |
| ASNS | ASXL1 | ATIC | ATM | ATP7B | ATR | ATRX | AURKA | AURKB | AXIN1 | AXIN2 |
| AXL | B2M | BAP1 | BARD1 | BCL2 | BCL2L1 | BCL2L11 | BCL6 | BCL7A | BCL10 | BCL11B |
| BCLAF1 | BCOR | BCORL1 | BCR | BIRC3 | BLM | BMPR1A | BRAF | BRCA1 | BRCA2 | BRD4 |
| BRIP1 | BTG1 | BTK | BUB1B | C3orf70 | C8orf34 | C10orf54 | C11orf30 | C11orf65 | CALR | CARD11 |
| CASP8 | CASR | CBFB | CBL | CBLB | CBLC | CBR3 | CCDC6 | CCND1 | CCND2 | CCND3 |
| CCNE1 | CD19 | CD22 | CD40 | CD70 | CD79A | CD79B | CD274 | CDC73 | CDH1 | CDK4 |
| CDK6 | CDK8 | CDK12 | CDKN1A | CDKN1B | CDKN1C | CDKN2A | CDKN2B | CDKN2C | CEBPA | CEP57 |
| CFTR | CHD2 | CHD4 | CHEK1 | CHEK2 | CIC | CIITA | CKS1B | CREBBP | CRKL | CRLF2 |
| CSF1R | CSF3R | CTC1 | CTCF | CTLA4 | CTNNA1 | CTNNB1 | CTRC | CUX1 | CXCR4 | CYLD |
| CYP1B1 | CYP2D6 | CYP3A5 | DAXX | DDB2 | DDR2 | DDX3X | DICER1 | DIRC2 | DIS3 | DIS3L2 |
| DKC1 | DNM2 | DNMT3A | DOT1L | DPYD | DYNC2H1 | EBF1 | ECT2L | EGF | EGFR | EGLN1 |
| ELF3 | ENG | EP300 | EPCAM | EPHA2 | EPHA7 | EPHB1 | EPHB2 | EPOR | ERBB2 | ERBB3 |
| ERBB4 | ERCC1 | ERCC2 | ERCC3 | ERCC4 | ERCC5 | ERCC6 | ERG | ERRFI1 | ESR1 | ETS1 |
| ETS2 | ETV1 | ETV4 | ETV5 | ETV6 | EWSR1 | EZH2 | FAM46C | FAM175A | FANCA | FANCB |
| FANCC | FANCD2 | FANCE | FANCF | FANCG | FANCI | FANCL | FANCM | FAS | FAT1 | FBXO11 |
| FBXW7 | FCGR2A | FCGR3A | FDPS | FGF1 | FGF2 | FGF3 | FGF4 | FGF5 | FGF6 | FGF7 |
| FGF8 | FGF9 | FGF10 | FGF14 | FGF23 | FGFR1 | FGFR2 | FGFR3 | FGFR4 | FH | FHIT |
| FLCN | FLG | FLT1 | FLT3 | FLT4 | FNTB | FOXA1 | FOXL2 | FOXO1 | FOXO3 | FOXP1 |
| FOXQ1 | FRS2 | FUBP1 | G6PD | GALNT12 | GATA1 | GATA2 | GATA3 | GATA4 | GATA6 | GEN1 |
| GLI1 | GNA11 | GNA13 | GNAQ | GNAS | GPC3 | GPS2 | GREM1 | GRIN2A | GRM3 | GSTP1 |
| H3F3A | H19 | HAS3 | HAVCR2 | HDAC1 | HDAC2 | HDAC4 | HGF | HIF1A | HIST1H1E | HIST1H3B |
| HIST1H4E | HLA-A | HLA-B | HLA-C | HLA-DMA | HLA-DMB | HLA-DOA | HLA-DOB | HLA-DPA1 | HLA-DPB1 | HLA-DPB2 |
| HLA-DQA1 | HLA-DQA2 | HLA-DQB1 | HLA-DQB2 | HLA-DRA | HLA-DRB1 | HLA-DRB5 | HLA-DRB6 | HLA-E | HLA-F | HLA-G |
| HNF1A | HNF1B | HOXB13 | HRAS | HSP90AA1 | HSPH1 | IDH1 | IDH2 | IDO1 | IFIT1 | IFIT2 |
| IFIT3 | IFNAR1 | IFNAR2 | IFNGR1 | IFNGR2 | IFNL3 | IKBKE | IKZF1 | IL2RA | IL6R | IL7R |
| IL10RA | IL15 | ING1 | INPP4B | IRF1 | IRF2 | IRF4 | IRS2 | ITPKB | JAK1 | JAK2 |
| JAK3 | JUN | KAT6A | KDM5A | KDM5C | KDM6A | KDR | KEAP1 | KEL | KIF1B | KIT |
| KLHL6 | KLLN | KMT2A | KMT2B | KMT2C | KMT2D | KRAS | LAG3 | LDLR | LEF1 | LMNA |
| LMO1 | LRP1B | LYN | LZTR1 | MAD2L2 | MAF | MAFB | MALT1 | MAP2K1 | MAP2K2 | MAP2K4 |
| MAP3K1 | MAP3K7 | MAPK1 | MAX | MC1R | MCL1 | MDM2 | MDM4 | MED12 | MEF2B | MEN1 |
| MET | MGMT | MIB1 | MITF | MKI67 | MLH1 | MLH3 | MLLT3 | MPL | MRE11A | MS4A1 |
| MSH2 | MSH3 | MSH6 | MTAP | MTHFR | MTOR | MTRR | MUTYH | MYB | MYC | MYCL |
| MYCN | MYD88 | MYH11 | NBN | NCOR1 | NCOR2 | NF1 | NF2 | NFE2L2 | NFKBIA | NHP2 |
| NKX2-1 | NOP10 | NOTCH1 | NOTCH2 | NOTCH3 | NPM1 | NQO1 | NRAS | NRG1 | NSD1 | NT5C2 |
| NTHL1 | NTRK1 | NTRK2 | NTRK3 | NUDT15 | NUP98 | P2RY8 | PAK1 | PALB2 | PALLD | PARK2 |
| PAX3 | PAX5 | PAX7 | PAX8 | PBRM1 | PCBP1 | PDCD1 | PDCD1LG2 | PDGFRA | PDGFRB | PDK1 |
| PDPK1 | PHF6 | PHOX2B | PIAS4 | PIK3C2B | PIK3CA | PIK3CB | PIK3CD | PIK3CG | PIK3R1 | PIK3R2 |
| PIM1 | PLCG2 | PML | PMS1 | PMS2 | POLD1 | POLE | POLH | POT1 | POU2F2 | PPP1R15A |

FIG. 13A

| PPP2R1A | PPP2R2A | PPP6C | PRCC | PRDM1 | PREX2 | PRKAR1A | PRSS1 | PRSS2 | PTCH1 | PTCH2 |
|---|---|---|---|---|---|---|---|---|---|---|
| PTEN | PTPN11 | PTPN13 | PTPN22 | PTPRD | QKI | RAC1 | RAD21 | RAD50 | RAD51 | RAD51B |
| RAD51C | RAD51D | RAD54L | RAF1 | RANBP2 | RARA | RASA1 | RB1 | RBM10 | RECQL4 | RET |
| RHOA | RICTOR | RINT1 | RIT1 | RNF43 | RNF139 | ROS1 | RPL5 | RPS6KB1 | RPS15 | RPTOR |
| RSF1 | RUNX1 | RUNX1T1 | RXRA | SCG5 | SDHA | SDHAF2 | SDHB | SDHC | SDHD | SEC23B |
| SEMA3C | SETBP1 | SETD2 | SF3B1 | SGK1 | SH2B3 | SLC26A3 | SLC47A2 | SLIT2 | SLX4 | SMAD2 |
| SMAD3 | SMAD4 | SMARCA1 | SMARCA4 | SMARCB1 | SMARCE1 | SMC1A | SMC3 | SMO | SOCS1 | SOD2 |
| SOX2 | SOX9 | SOX10 | SPEN | SPINK1 | SPOP | SPRED1 | SRC | SRSF2 | STAG2 | STAT3 |
| STAT4 | STAT5A | STAT5B | STAT6 | STK11 | SUFU | SUZ12 | SYK | TAF1 | TANC1 | TAP1 |
| TAP2 | TBC1D12 | TBL1XR1 | TBX3 | TCF3 | TCF7L2 | TCL1A | TERT | TET2 | TGFBR2 | TIGIT |
| TMEM127 | TMEM173 | TMPRSS2 | TNF | TNFAIP3 | TNFRSF9 | TNFRSF14 | TNFRSF17 | TOP1 | TOP2A | TP53 |
| TP63 | TPM1 | TPMT | TRAF3 | TSC1 | TSC2 | TSHR | TUSC3 | TYMS | U2AF1 | UBE2T |
| UGT1A1 | UGT1A9 | UMPS | VEGFA | VHL | WEE1 | WHSC1 | WRN | WT1 | XPA | XPC |
| XPO1 | XRCC1 | XRCC2 | XRCC3 | YEATS4 | ZFHX3 | ZNF217 | ZNF471 | ZNF620 | ZNF750 | ZNRF3 |
| ZRSR2 | | | | | | | | | | |

FIG. 13B

CALCULATING CELL-TYPE RNA PROFILES FOR DIAGNOSIS AND TREATMENT

CROSS REFERENCE TO RELATED APPLICATIONS

This application claims priority to U.S. Provisional Patent Application No. 62/924,054, filed on Oct. 21, 2019, the contents of which is hereby incorporated by reference in its entirety for all purposes.

TECHNICAL FIELD

The present disclosure relates to generating and applying RNA profiles to identify cell types and their proportions in patient samples, to improve precision of treatment selection and monitoring.

BACKGROUND

Acquisition and analysis of genetic information of subjects through genetic testing in the field of next-generation sequencing ("NGS") for genomics is a rapidly evolving field. NGS involves using specialized equipment, such as a next-generation gene sequencer, which is an automated instrument that determines the order of nucleotides in DNA and/or RNA. The instrument reports the sequences as a string of letters, called a read. These reads allow the identification of genes, variants, or sequences of nucleotides in the human genome. An analyst compares these reads from genes to one or more reference genomes of the same genes, variants, or sequences of nucleotides. Identification of certain genetic mutations or particular variants plays an important role in selecting the most beneficial line of therapy for a patient.

Pharmacogenomics is the study of the role of the human genome in drug response. Aptly named by combining pharmacology and genomics, pharmacogenomics analyzes how the genetic makeup of an individual affects their response to drugs. It deals with the influence of genetic variation on drug response in patients by correlating gene expression pharmacokinetics (drug absorption, distribution, metabolism, and elimination) and pharmacodynamics (effects mediated through a drug's biological targets). The term pharmacogenomics is often used interchangeably with pharmacogenetics. Although both terms relate to drug response based on genetic influences, pharmacogenetics focuses on single drug-gene interactions, while pharmacogenomics encompasses a more genome-wide association approach, incorporating genomics and epigenetics while dealing with the effects of multiple genes on drug response. This information may assist medical professionals in choosing which treatment to prescribe to a patient.

RNA sequencing has become a valuable tool for transcriptome-wide analysis of differential gene expression and differential splicing of mRNAs. RNA sequencing methods are used for single-cell and multi-cell gene expression analysis. A challenge in interpreting RNA sequencing information and isolating biomarkers for disease susceptibility and/or pharmacogenomic effects is rooted in a lack of structured information between the human genome and patient/clinical information such as, e.g., disease progression and treatment information. While many projects are ongoing worldwide to identify affordable, scalable single-cell sequencing techniques, a viable solution has yet to be implemented in commercial practice.

Accordingly, there is a need in improved tools for analysis and interpretation of genetic and clinical patient data, including bulk-cell sequencing data, to make inferences about diagnosis of a disease or condition and its state, disease susceptibility, and pharmacogenomics and thereby make appropriate treatment decisions, which can improve overall patient healthcare.

SUMMARY

In some embodiments, methods are provided for analyzing RNA sequencing and imaging data from multiple biological samples to generate cell-type RNA profiles for cell types, and to apply the cell-type RNA profiles to a new (test) biological sample obtained from a patient to determine a cell type composition of the patient. The ability to determine a cell type composition (e.g., a cancer composition) may be used in various clinical applications. The present disclosure provides a more precise analysis of a sample composition than existing approaches.

In embodiments of the present disclosure, the methods can identify known cell types, as well as unknown cell types, for cell types in various tissues and at different stages of cell maturation. Each cell type may be represented by a respective cell-type RNA profile that defines gene expression (abundance) levels for each gene in a plurality of genes for that cell-type RNA profile. In some embodiments, the gene expression levels for each gene in a cell-type RNA profile are modeled as a distribution, such as, for example, a gamma, normal, or another distribution.

In embodiments, each sample, such as, e.g., a pathology slide or any other form having a boundary, is modeled as a sum of parts with their percentage summing up to 100% (or 1, if proportions are used). This constraint allows applying machine-learning algorithms to generate and train models until convergence to an optimal solution in a time-efficient manner. In this way, a number of cell types, their respective profiles, and their proportions that accurately describe a sample composition are identified.

In some aspects, a method for determining a cancer composition of a subject is provided which in some embodiments includes, at a computer system having one or more processors and memory storing one or more programs for execution by the one or more processors, generating, in electronic form, for each respective genetic target in a first plurality of genetic targets, a corresponding shape parameter, the first plurality of genetic targets obtained based on RNA sequencing of one or more respective biological samples obtained from a respective tumor specimen of each respective subject across a plurality of subjects. The method further includes, obtaining, in electronic form, for each respective subject across the plurality of subjects, a corresponding relative proportion of one or more sets of cell types in a plurality of sets of cell types; obtaining, in electronic form, for each respective subject across the plurality of subjects, for each respective genetic target in the first plurality of genetic targets, a corresponding measure of central tendency of an abundance of the respective genetic target; and refining a first optimization model subject to a first plurality of constraints. The first plurality of constraints include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects, the refining thereby identifying a plurality of calculated cell types in a first set of cell types in the plurality of sets of cell types, the refining further generating a respective calculated cell type RNA expression profile for each calculated cell type in the plurality of calculated cell types.

The method further comprises using the respective calculated cell type RNA expression profile for each calculated cell type in the plurality of calculated cell types to determine a cancer composition of a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is an illustration of an example of a statistical analysis approach in RNA profiling.

FIG. 7 is a diagram illustrating a method of generating of cell-type RNA profiles from information on a pathology slide, in accordance with some embodiments of the present disclosure.

FIG. 8 is a flow chart illustrating a process of generating cell-type profiles, in accordance with some embodiments of the present disclosure.

FIGS. 10A, 10B, and 10C collectively provide a flow chart of processes and features for determining a cancer composition of a subject, in accordance with some embodiments of the present disclosure.

FIGS. 13A and 13B collectively provide a list of example genes that are informative for determining a cancer composition of a subject, in accordance with some embodiments of the present disclosure.

Like reference numerals may refer to corresponding parts throughout the several views of the drawings, in accordance with some embodiments of the present disclosure.

DETAILED DESCRIPTION

Figure 1A:
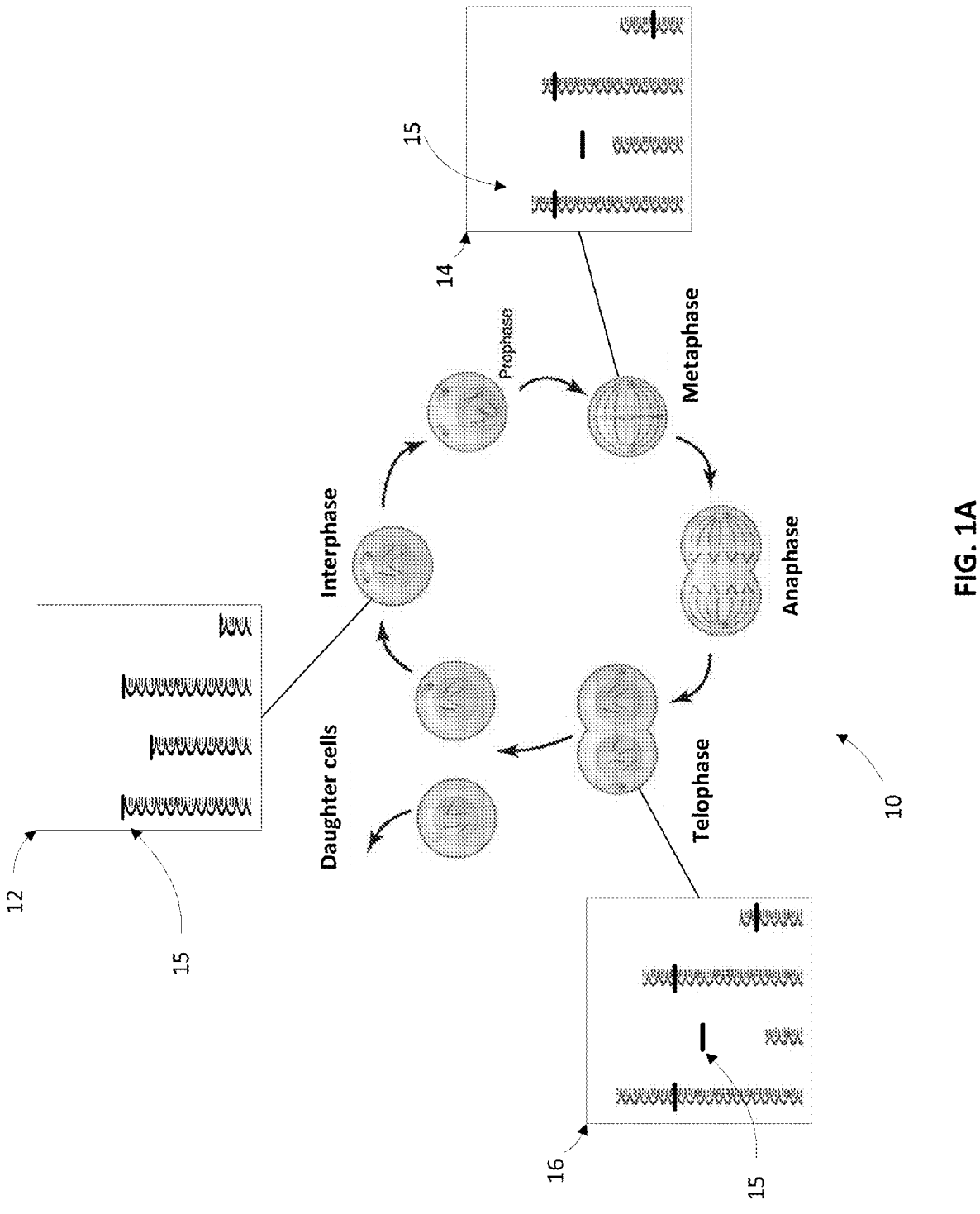
FIG. 1A is a diagram illustrating a challenge in RNA profiling of sequencing information.

Embodiments of the present disclosure relate to identifying cell-type RNA profiles based on data (e.g., RNA sequencing, imaging data, etc.) acquired from patients' samples. One or more models can be trained to identify a type, number, and proportion of cell-type RNA profiles in a patient's sample. The identification of the cell-type RNA profiles for the patients in accordance with embodiments of the present disclosure may improve clinical diagnosis, and may facilitate selection and monitoring of treatments of various conditions and diseases, as well as improve the overall standard of care. Embodiments of the present disclosure may allow enhancing existing sequencing procedures and removing unknown variance in patient diagnosis and treatment, particularly in cases impacted by varying tumor purities in a specimen.

The human genome was mapped in April 2003 by the Human Genome Project and opened the door for progress in numerous fields of study focused on the sequence of nucleotide base pairs that make up human DNA. The human genome has over six billion of these nucleotides packaged into two sets of twenty-three chromosomes, one set inherited from each parent, encoding over thirty-thousand genes. The order in which the nucleotide types are arranged is known as the molecular sequence, genetic sequence, or genome. DNA strands guide the production of proteins for each cell by acting as a code or a template for the protein synthesis process. These proteins are catalysts for important bodily functions and fill roles such as influencing drug absorption or driving immune response for a patient. During protein synthesis DNA strands undergo a transcription process, where they are temporarily unraveled to create RNA by transcription, and then the RNA is translated to a protein strand. Through cataloging the RNA that translates into important proteins, treatment selections may be improved for each patient.

The capture of patient genetic information through genetic testing in the field of next-generation sequencing ("NGS") for genomics is a new and rapidly evolving field. NGS involves using specialized equipment such as, e.g., a next-generation gene sequencer, which is an automated instrument that determines the order of nucleotides in DNA and/or RNA. The instrument can report the sequences as a string of letters, called a read. These reads allow the identification of genes, variants, or sequences of nucleotides in the human genome. The reads from genes can be compared to one or more reference genomes of the same genes, variants, or sequences of nucleotides. Identification of certain genetic mutations or particular variants can play an important role in selecting the most beneficial line of therapy for a patient.

The challenge in interpreting RNA sequencing information and isolating biomarkers for disease susceptibility and/or pharmacogenomic effects is rooted in a lack of structured information on relationships between the human genome and patient/clinical information such as, e.g., disease progression and treatment information. A bulk-cell sequencing analysis of a tissue specimen, using scraping a slide of a tumor, has been used for gathering sequencing information relating to an individual patient. At the same time, scraping a slide for bulk-cell sequencing has a number of challenges that hinder the acquisition of reliable results, including tumor-only results. This is exacerbated by the lack of techniques for identifying RNA cell types and their respective cell-type profiles.

FIG. 1A, which is an annotated illustration of a mitosis cell cycle 10 (Miller-Keane Encyclopedia and Dictionary of Medicine, Nursing, and Allied Health, Seventh Edition (2003)), illustrates a challenge in RNA cell-profiling from multi-cell sequence information. Sequencing a patient's genome delivers what is effectively a snapshot of the state of the tissue, such as a tumor, as it existed at the time of extraction. However, during a cell's life cycle, the cell is not a static entity as it is changing and evolving. For example, as shown schematically in FIG. 1A, a cell undergoing the mitosis cell cycle 10, in its resting state (interphase) may have an RNA expression profile 12 (wherein an RNA expression profile represents abundance of RNAs), such that each gene which an RNA expression read may be mapped to will have a certain expression level. For illustrative purposes, the RNA expression profile 12 represents four genes (unlabeled) having different expression levels, though a person of ordinary skill in the art would recognize that the RNA expression profile may be across more than 20,000 genes or across a smaller, more selective subset of genes. A cell may begin mitosis by proceeding through prophase where the cell prepares for the process of division by replicating DNA and beginning to align the centrioles of the cell at opposite poles in the cell. Continuing through mitosis, the cell may proceed through metaphase where the DNA is lined up along a central axis of the cell. As shown by way of example in FIG. 1A, in the metaphase, represented by an RNA expression profile 14, the four genes may have respective RNA expression levels that are different from these genes' expression levels in the RNA expression profile 12. In some cases, variations may occur due to, e.g., doubling of the DNA, potentially leading to more protein synthesis. However, other cellular functions are affecting RNA transcription. For example, during mitosis, a synthesis of certain proteins may be inhibited, while a synthesis of other proteins may be activated. Subsequently, the associated genes, which were previously active, may not be instructed to produce additional proteins, while the cell may be producing proteins from the newly activated genes such that the cell's state may be represented by the unique RNA profile 14 while undergoing metaphase, different from the RNA profile 12 representing the gene expression during interphase. An RNA profile 16 represents gene expression during telophase.

As used herein, the "cell-type RNA profile" may also be referred to as an RNA expression profile or cell-type RNA expression profile for a respective cell type that allows the cell type to be identified in RNA expression data. Also, RNA expression (or RNA expression levels) is used herein interchangeably with RNA abundance, and they represent gene expression. However, as a person of skill in the art would understand, measured RNA abundance and RNA expression may be different in some circumstances.

In FIG. 1A, RNA expression levels in the RNA profile 12 are shown by identifiers 15, and the identifiers 15 are also shown in connection with the RNA profile 14 and the RNA profile 16. In this way, deviations in cell's RNA expression levels at the metaphase and telophase from cell's RNA expression levels in the interphase are visualized. The identifiers 15 may indicate baseline RNA expression levels. For example, as certain proteins are no longer synthesized, RNA expressions may decrease slightly as the residual RNA breaks down. Additionally, as other proteins are being synthesized in greater numbers, RNA abundance may increase slightly. As the cell proceeds through mitosis, the chromosomes may separate and begin to attract to opposing centromeres during anaphase. Near the completion of mitosis, the cell division is finishing and the cell membrane may begin separating into two separate cells. While undergoing the final process, telophase, the cell RNA abundance may be represented by the RNA profile 16.

An RNA profile shows RNA expressions consistent with inhibited protein synthesis as well as the RNA expressions consistent with activated protein synthesis. Additionally, some RNA expression may be the same as the cell maintains similar functions throughout each phase of mitosis. Through careful observation, distinct RNA profiles may be established which identify a single cell at different phases as it progresses through mitosis. While the foregoing example depicts unique RNA expression profiles at the interphase, metaphase, and telophase stages of mitosis, it should be appreciated that phases during the cell cycle can be represented by various other RNA profiles.

Figure 1B:
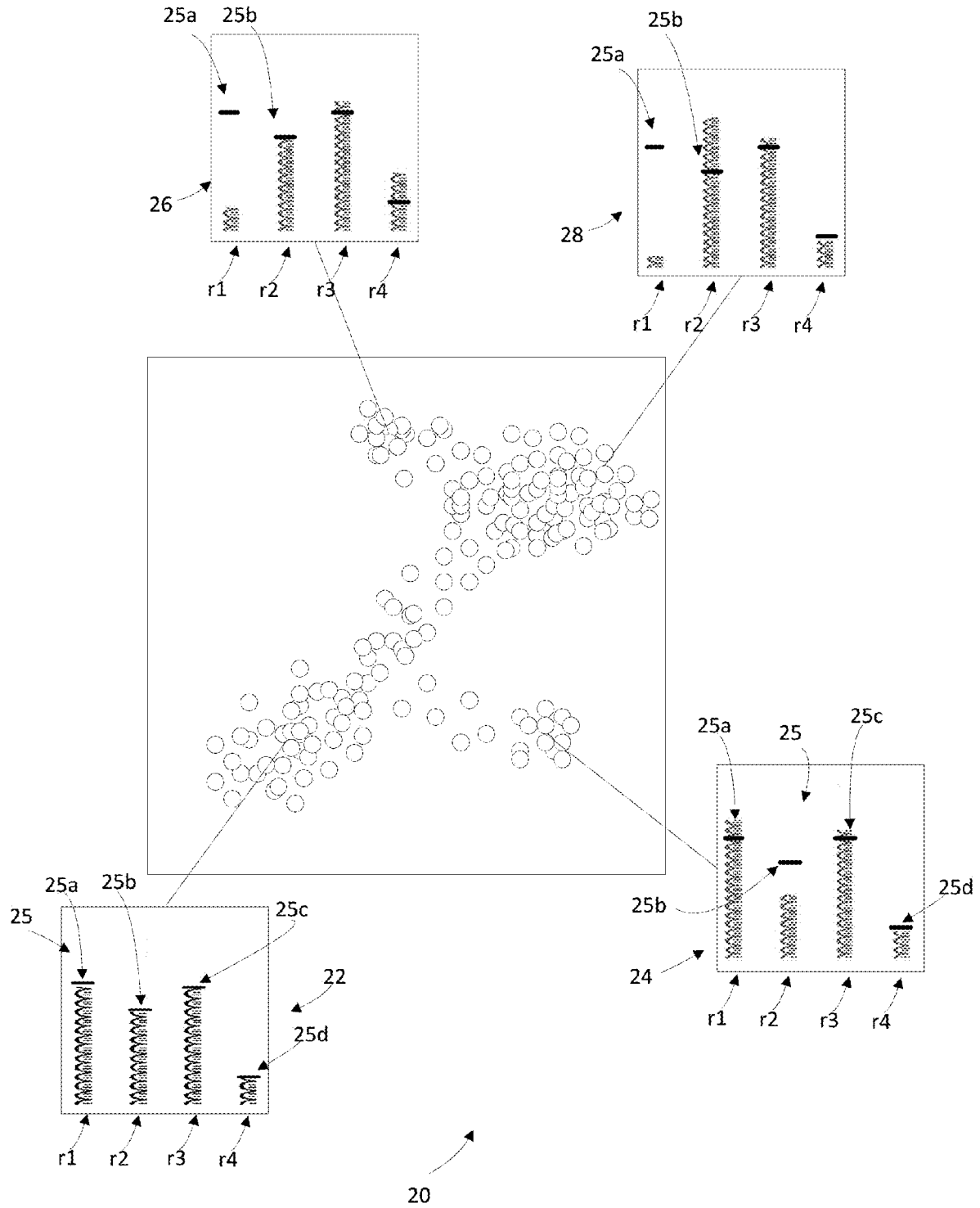
FIG. 1B is another diagram illustrating a challenge in RNA profiling of sequencing information.

FIG. 1B illustrates schematically another challenge in RNA cell profiling from multi-cell sequence information. Certain cell types mature from a first cell type into a second cell type over time. For example, immune cells, such as, e.g., T-cells or B-cells, start off as base pluripotent hematopoietic stem cells (HSCs) and mature into a plethora of distinct progenitors, including common lymphoid progenitors (CLPs). CLPs, just as the HSCs before them, may mature into a myriad of cells, such as dendritic cells (DCs), natural killer cells (NKs), B-cells, T-cells, and more. The immune B and T-cells are lymphocytes commonly found at the site of cancerous tumor cells. As immune cells, T-cells have the ability to make any shape of receptors which allow the cell to target specific antigens for destruction. B-cells generate antibodies and maintain a memory of antibodies which may be needed to protect against a subsequent infection. Other T-cells may stimulate the B-cell production of antibodies. Each matured version of B and T-cells may be represented by a respective unique RNA profile. At different points of cell maturation and division, immune cells of cytotoxic, memory, suppressor, and helper categories may have their own functions and RNA profiles.

A diagram 20 in FIG. 1B, illustrating schematically a cell maturation graph, shows by way of example natural divergence from an RNA expression profile 22 representing a common lymphoid progenitors (CLP) cell type. For illustrative purposes, the RNA expression profile 22 represents RNA expression levels or RNA abundance corresponding to four genes (r1, r2, r3, and r4) of varying expression. However, a person of ordinary skill in the art would recognize that the RNA expression profile may be across any number of genes, including 10, 100, 100, 10,000, 20,000 or more than 20,000 genes. As cells mature from the CLP cell type to the B-cell type, a branch may develop in the cell maturation graph corresponding to an RNA expression profile 24 which is distinct from the RNA expression profile 22. The differences in RNA expression levels among the RNA profiles 22 and 24 are shown by identifiers 25 in FIG. 1B. The identifiers 25, also shown in connection with RNA profiles 26 and 28 (additionally illustrating cell types present in this example), indicate baseline levels of RNA expression of the RNA expression profile 22. For example, identifiers 25a, 25b, 25c, 25d indicate a level of expression (abundance) of RNAs r1, r2, r3, and r4 in RNA expression profile 22, respectively. The identifiers 25a, 25b, 25c, 25d are also shown in connection with the RNA expression profile 24, where they, like in the RNA expression profile 22, indicate the level of expression of the RNAs r1, r2, r3, and r4. Respective bars illustrating expression levels of the RNAs r1, r2, r3, and r4 in the RNA expression profile 24 visualize, in connection with the identifiers 25a, 25b, 25c, 25d, a degree to which the expression levels of RNAs r1, r2, r3, and r4 are different in the RNA expression profile 24 as compared to the RNA expression profile 22.

A B-cell having RNA expression profile 24 may present with a noticeable decrease in gene expression for some genes while maintaining fairly consistent expression levels across other genes in comparison to the base CLP cell type. As shown in the example of FIG. 1B, other branches may be present in the cell maturation graph 20, such as a branch for suppressor T-cells (having the RNA expression profile 28) and a branch for cytotoxic T-cells (having the RNA expression profile 26). T-cells, as a whole, may be commonly identified from a substantial decrease in a particular gene expression, and their types may be differentiated one from another through observation of other gene expression differences. Furthermore, both B and T-cells may maintain fairly consistent gene expression in certain genes due to their common lineage from the CLP cell type and their function as immune cells.

As shown in FIGS. 1A and 1B, identifying and understanding RNA expression profiles in various cells is a challenging task. Cells are ever evolving, maturing to another cells, and are frequently undergoing mitosis to replicate. For example, when a T-cell finds antigens that it can bind to, it may quickly replicate itself in an offensive against the abnormal cells that were detected. At the same time, other T-cell types and B-cells types may also join in the offensive against the abnormal cells. A biopsy of a cancerous tumor may capture each of these immune, lymphoma cells, tumor cells, as well as other cell-types such as epithelium, stroma, muscle, fat, glial, and supporting cells. Each organ in the human body has a unique distribution of cells forming that organ. Biopsies taken from breast, colon, brain, lung, or other tumor sites may have a unique cell distribution while at the same time having cells that are common to each site.

Figure 2:
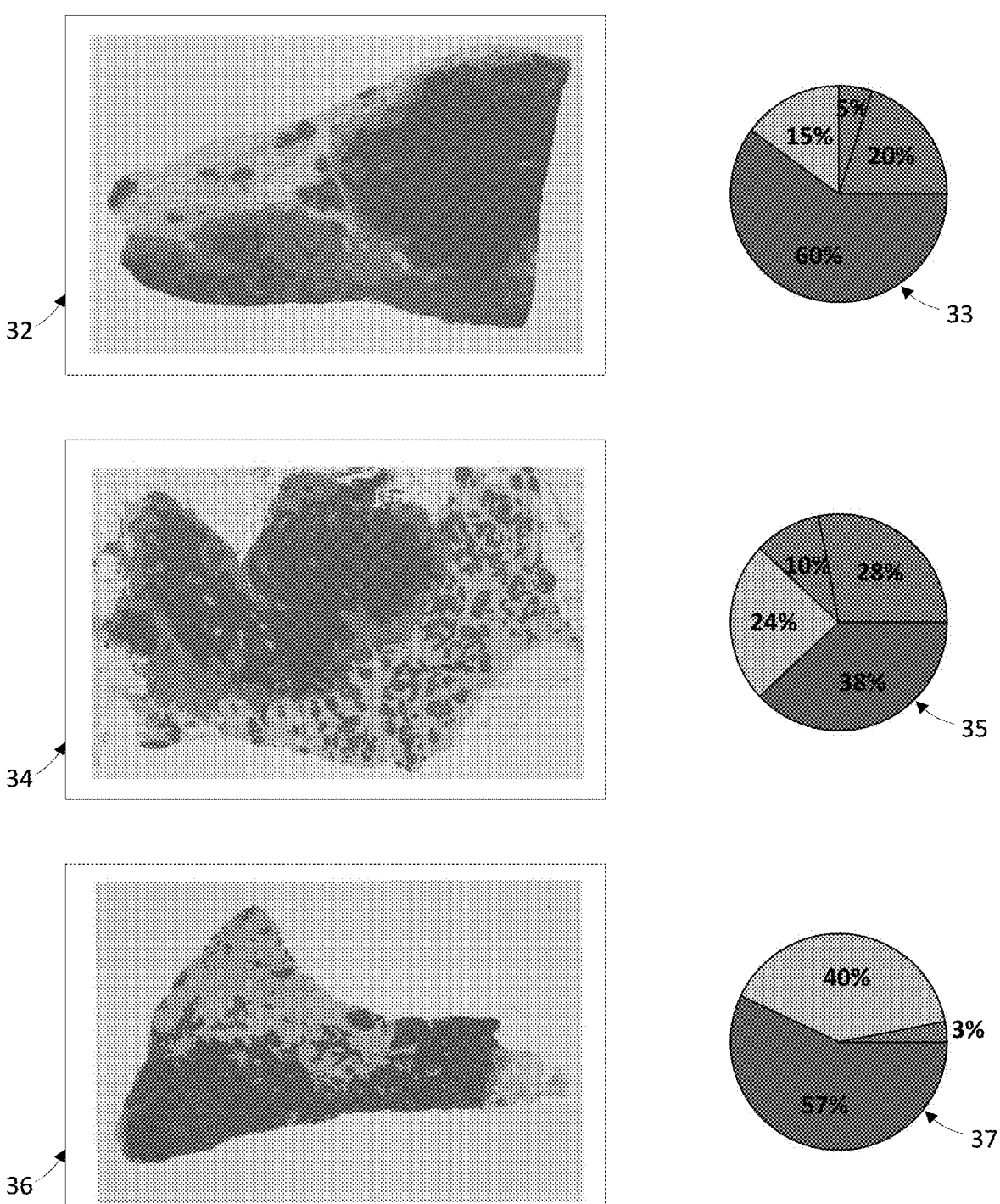
FIG. 2 is a further diagram illustrating a challenge in RNA profiling of sequencing information.

FIG. 2 illustrates an example of another challenge in RNA profiling from multi-cell sequence information including three breast tumor pathology slides 32, 34, and 36 that may be scraped for bulk cell sequencing. For example, the slide 32 is a breast tumor biopsy slide including a collection of tumor tissue (red), lymphocytes (purple), stroma (light green), and epithelium (dark green). A pathologist may review the slide 32 and identify a diagnosis in a pathology report including specific details of a grade of a tumor (in comparison to healthy cells) present, or varying levels of lymphovascular, perineural, or margin invasion present in the slide tissue. For example, a report may identify: 16% Tumor (with lymphocyte), 52% Tumor (with no lymphocyte), 6% Lymphocyte, 4% Stroma (with lymphocyte), 18% Stroma (with no lymphocyte), 1% Epithelium (with lymphocyte), 3% Epithelium (with no lymphocyte). As another example, pathology reports may identify tumor, stroma, lymphocytes, and epithelium percentages as a whole. An exemplary percentile breakdown for the slide 32 is shown in a pie chart 33 indicating 60% tumor, 15% stroma, 20% lymphocytes, and 5% epithelium. Bulk cell sequencing from a slide scrape of the slide 32 can be impacted by 40% of the sequenced tissue being non-tumor tissue.

Further exacerbating the accuracy and reliability of analysis and clinical use of the sequencing data is the fact that two or more of cell types present in a pathology slide may be at different stages of cell maturation and may also be at different stages of their individual life cycles, including mitosis. Ultimately, precision medicine concerns targeting the patient's tumor, but the traditional bulk cell sequencing introduces a substantial amount of noise by allowing other tissue RNA expression to cloud the results. Traditional approaches that merely account for tumor/non-tumor percentage may thus not be accurate enough to allow making correct inferences about diagnosis and treatment.

A pathology slide 34 in FIG. 2 represents a breast tumor biopsy of another patient. Unlike in the slide 32 where the majority of the tissue scraped is tumor tissue, the slide 34 has 38% of tumor tissue, and 62% of a non-tumor tissue encompassing 28% lymphocytes, 24% stroma, and 10% epithelium, as shown in the chart 35. A slide 36 represents yet another example of a pathology slide comprising 57% tumor, 40% stroma, and 3% lymphocytes, without observable traces of epithelium, as shown in a chart 37. It should be noted that cell types' percentages are shown in FIG. 2 for illustration purposes only, and that these percentages can be approximate.

Accounting for different ratios of tumor tissue(s) to non-tumor tissue(s), for different stages of maturation of each cell, and for different stages of the cell cycle, in order to reliably identify tumor-specific RNA expression profiles, are challenging tasks.

Accordingly, embodiments of the present disclosure provide methods for determining a cancer composition of a biological sample obtained from a subject (also referred to as a cancer composition of a subject), which include improved approaches for identifying cell types present in the sample and percentages of the cell types. A model of one or more RNA profile for each cell and/or tissue type may be generated, and the model may be used to determine cell types and their proportions in patient samples.

In embodiments in which single-cell sequencing is used and gene expression values are available, methods in accordance with embodiments of the present disclosure allow determining respective proportions of cell types in a biological sample.

In the described embodiments, RNA data in a sample (e.g., a sample on a pathology slide) is modeled as a sum of parts. For instance, a part may be a tissue type present in a sample. More than one model can be generated and trained for each tissue type, e.g., according to a tissue site, cancer type, etc. In some embodiments, a single model can be generated for some tissue types, whereas multiple models are generated for other tissue types. The models can be generated based on known cell-type RNA profiles for tissue types. Also, a model can be generated that is able to identify unknown cell/tissue types. Thus, the described techniques can take into account effects of the extraneous tissue types and use the remaining tissue types to derive knowledge about unknown tissue types, including tumor and non-tumor tissue types.

In some embodiments, gene expression data is modeled by gamma distributions. Also, in some embodiments, cell type percentages are determined as being greater than zero and, for a biological sample in any form, the percentages sum to 100%. In some embodiments, a gamma distribution is mapped to each gene for each tissue type. Mean and shape parameters of a gamma distribution can be calculated, and the method may fit across all percentages of tissue type to all mean and shape parameters, to find the best fit.

In some embodiments, a model can be applied to a new tumor RNA sequence obtained from a sample to predict one or more of a percentage of a tumor present in the sample, percentages of tissue types present, a type of tumor present, and RNA expression of only the tumor. The model can generate what is referred to herein as a sum of parts, wherein each part of the percentage is iteratively estimated using the model. Each part in the sum of parts can be individually balanced according to the mean and shape parameters of the gamma distribution. Accordingly, expression data for each gene can be iteratively balanced with expression data for of every other gene according to the mean and shape of the gamma distribution model until the best fit for the present cell types and their respective percentages (or proportions) are calculated.

In some embodiments, for each biological sample used to train a model (referred to as a first optimization model, in some embodiments), a corresponding relative proportion of one or more sets of cell types in a plurality of sets of cell types can be obtained. For example, the relative proportions may be obtained based on a pathology report (e.g., based on imaging analysis) or a report generated based on any other approach. In some cases, a pathology report may include percentages and types of the tissue(s) observed in the sample.

In some embodiments, a method for determining a cancer composition of a subject is provided that comprises, at a computer system having one or more processors and memory storing one or more programs for execution by the one or more processors, generating, in electronic form, for each respective genetic target in a first plurality of genetic targets (e.g., RNA expression data, transcriptome data, or any other type of data), a corresponding shape parameter (e.g., in some embodiments, a shape parameter for a gamma distribution used to model gene expression data). The first plurality of genetic targets can be obtained based on RNA sequencing of one or more respective biological samples obtained from a respective tumor specimen of each respective subject across a plurality of subjects. The method comprises obtaining, in electronic form, for each respective subject across the plurality of subjects, a corresponding relative proportion of one or more sets of cell types in a plurality of sets of cell types; obtaining, in electronic form, for each respective subject across the plurality of subjects, for each respective genetic target in the first plurality of genetic targets, a corresponding measure of central tendency of an abundance of the respective genetic target (e.g., in some embodiments, a mean parameter for a gamma distribution used to model gene expression data).

The method further comprises refining a first optimization model subject to a first plurality of constraints that may include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects. The refining of the first optimization model identifies a plurality of calculated cell types in a first set of cell types in the plurality of sets of cell types, and a respective calculated cell type RNA expression profile is thus generated for each calculated cell type in the plurality of calculated cell types.

The thus refined, or trained, first optimization model can be used to determine a cancer composition of a subject, as discussed in more detail below.

Figure 3:
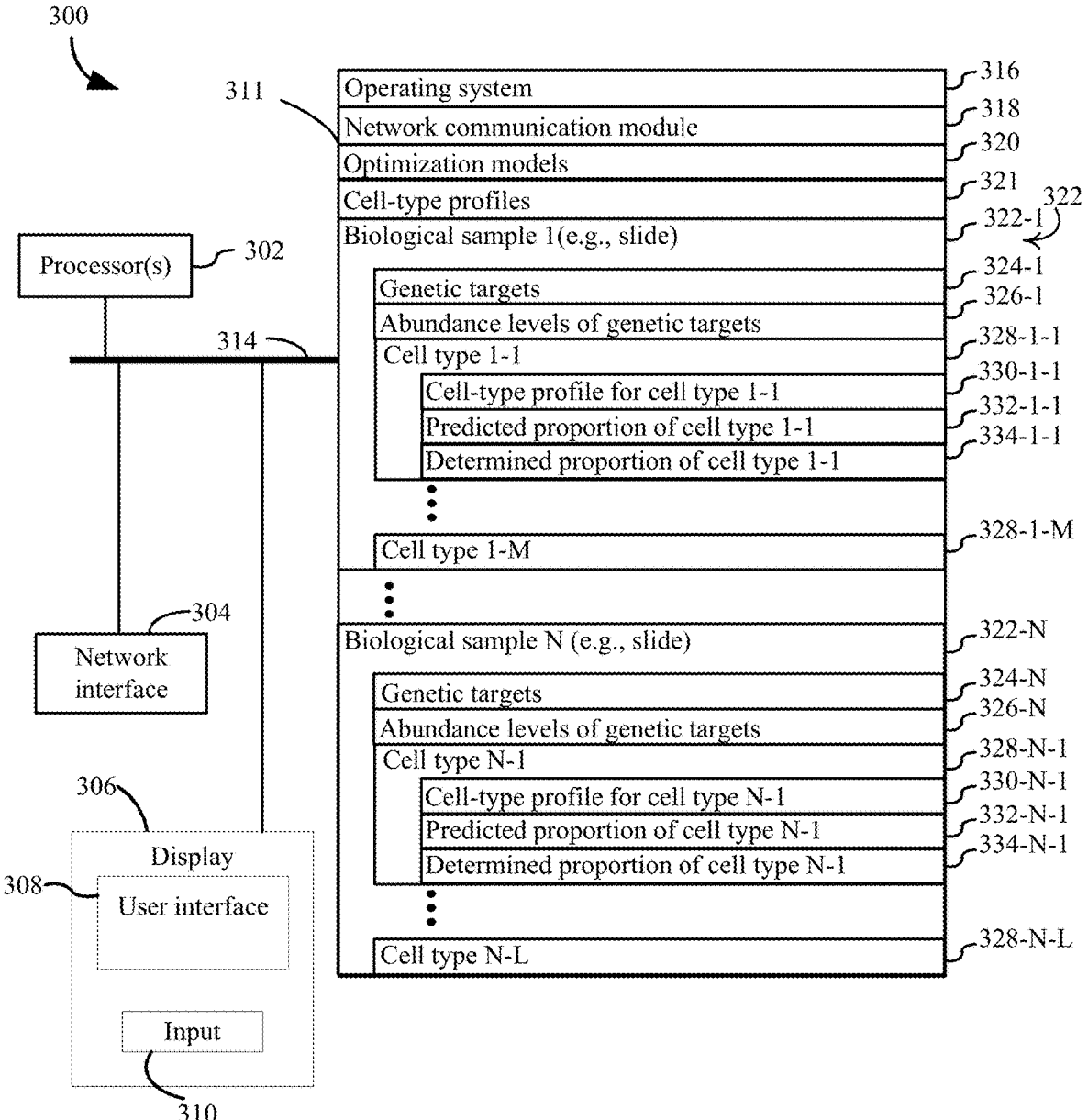
FIG. 3 is a block diagram illustrating an example computing device, in accordance with some embodiments of the present disclosure.

Details of an exemplary system in which some embodiments can be implemented are described in conjunction with FIG. 3. FIG. 3 is a block diagram illustrating a system 300 in accordance with some implementations of the present disclosure. The system 300 in some implementations includes one or more hardware processing units CPU(s) 302 (at least one processor), one or more network interfaces 304, a display 306 configured to present a user interface 308, and an input system 310, memory 311 (non-persistent, persistent, or any combination thereof), and one or more communication buses 114 for interconnecting these components. The one or more communication buses 314 optionally include circuitry (sometimes called a chipset) that interconnects and controls communications between system components.

In embodiments in which memory 311 is non-persistent, it typically includes high-speed random access memory, such as DRAM, SRAM, DDR RAM, ROM, EEPROM, flash memory, whereas the persistent memory typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The memory 311 optionally includes one or more storage devices remotely located from the CPU(s) 302. In embodiments in which memory 311, or one or more of its parts, are persistent memory and includes non-volatile memory device (s), the memory comprises at least one non-transitory computer readable storage medium. In some implementations, as shown in the example of FIG. 3, the non-persistent memory 311, or alternatively the non-transitory computer-readable storage medium, stores the following programs, modules and data structures, or a subset thereof (sometimes in conjunction with the persistent memory):

an optional operating system 316, which includes procedures for handling various basic system services and for performing hardware dependent tasks;

an optional network communication module (or instructions) 318 for connecting the system 300 with other devices and/or a communication network via the network interface 304;

an optimization models module 320 that is configured to generate, train, and control storing of a plurality of optimization models each configured to identify within genetic data (e.g., gene expression data, RNA expression or abundance data, etc.) cell types based on respective cell-type profiles;

cell-type profiles module 321, which can be part of the module 320 for generating and training the optimization models, and which is shown separately for illustrating purposes only, to show that the optimization models are built to identify cell types based on respective cell-type profiles;

data on a plurality of biological samples 322 shown by way of example to include a biological sample 322-1, . . . , biological sample 322-N; wherein the sample 322-1 is associated with genetic targets 324-1, respective abundance levels 326-1 of the genetic targets 324-1, and a plurality of cell types; and the sample 322-N is associated with genetic targets 324-N, respective abundance levels 326-N of the genetic targets 324-N, and a plurality of cell types;

the plurality of cell types for the biological sample 322-1 (e.g., cell type 1-1 (328-1-1), . . . , cell type 1-M (328-1-M)), wherein the cell type 1-1 (328-1-1) associated with a cell-type profile 330-1-1, a predicted proportion 332-1-1 of the cell type 1-1 in the sample 322-1 (e.g., based on a pathology report or based on another cell counting technique), and a determined proportion 334-1-1 of the cell type 1-1 in the sample 322-1;

the plurality of cell types for the biological sample 322-N(e.g., cell type N-1 (328-N-1), . . . , cell type N-L (328-N-L), wherein the cell type N-1 (328-N-1) is associated with a cell-type profile 330-N-1, a predicted proportion 332-N-1 of the cell type N-1 in the sample 322-1 (e.g., based on a pathology report or based on another cell counting technique), and a determined proportion 334-N-1 of the cell type N-1 in the sample 322-N.

It should be appreciated that the plurality of biological samples 322 can be obtained from a plurality of subjects such that a biological sample is obtained from a respective subject. Also, although not shown in FIG. 3, each biological sample from the plurality of biological samples 322 can be associated with various other information that may be stored in the memory 311, including patient's information such as demographic, clinical, and other characteristics.

In some embodiments, more than one sample is obtained from a subject—for example, more than one tissue slice can be taken that are adjacent to each other. In some cases, the tissue slices are obtained such that some of the pathology slides prepared from the respective slices are imaged, whereas some of the pathology slides are used for obtaining sequencing information.

In FIG. 3, the data relating to the biological samples 322 are shown to be associated with more than one cell type. It should be appreciated that biological samples may include different numbers of cell types, as shown schematically in FIG. 3 where the sample 322-1 includes M cell types, and the sample 322-N includes L cell types. In some cases, samples collected from a certain patient (e.g., from different tissue types, body sites, samples collected at different times, etc.) may differ by at least one cell type. In general, embodiments of the present disclosure are not limited to any specific type of a biological sample or to a number and types of cell types that can be identified in the samples.

In various implementations, one or more of the elements identified above in connection with FIG. 3 may be stored in one or more of the previously mentioned memory devices, and correspond to a set of instructions for performing functions described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 311 optionally stores a subset of the modules and data structures identified above. Furthermore, in some embodiments, the memory stores additional modules and data structures not described above. In some embodiments, one or more of the above identified elements are stored in a computer system, other than the computer system 300 and that are addressable by the computer system 300 so that the system 300 may retrieve all or a portion of such data when needed.

It should be appreciated that FIG. 3 depicts the system 300 as a functional description of the various features of the present disclosure that may be present in computer systems. As a person of skill in the art would understand, some of components and modules shown separately can be combined in a suitable manner. Also, some or all of these modules may be stored in a non-persistent memory or persistent memory, or in more than one memory. For example, in some embodiments, the optimization models 320 and/or information on the biological samples 322 may be stored in a remote storage device which can be a part of a cloud-based infrastructure. Any other components can be stored in remote storage device(s).

FIG. 4 illustrates examples of statistical analysis approaches that can account for multiple cell types present in RNA expression sequencing information. For example, in a simplistic representation of a graph 410, two cell types A and B may be present in an example of RNA sequencing information. A cell of cell type A may have an RNA expression profile, and a cell of cell type B may have a different respective RNA expression profile. Conceptually, a sequencing performed on a combination of cell types A and B may be represented in the graph 410. For example, an RNA expression profile of a pure cell type A may be represented as 100% cell type A and 0% cell-type B, and, conversely, an RNA expression profile of a pure cell type B may be represented as 100% cell type B and 0% cell type A. A mixture of cell types A and B may be similarly plotted along the graph. For example, sequencing information having 40% cell type A and 60% cell type B may be represented as: $E(A)*P(A)+E(B)*P(B)$, where $E(x)$ is an expected value of x and $P(x)$ is the proportion of x. In this example, an expected value of x is the cell-type RNA profile of x, and a proportion of x is an observed proportion of x in the whole. Continuing with this example, values for $P(A)$ and $P(B)$ are known: $E(A)*0.4+E(B)*0.6$, and a linear combination of the RNA profiles for the cell types A and B may be represented. The case may also arise where the cell-type RNA profiles for the cell types A and B are not known in advance; however, given enough RNA sequence information comprising differing proportions of the cell type A to the cell type B, RNA profiles for cell types A and B may be regressed from the combination of data.

In some embodiments, RNA sequencing information includes information on multiple cell types. The procedure described above for the two cell types A and B can be applied to multiple cell types as well. For example, a diagram 420 shows four cell types A, B, C, and D, in which case a combination of proportions of the cell types may be found on the surface or inside of a resulting four-sided polyhedron or tetrahedron 421, but not outside of the bounds of the polyhedron. These constraints may be a requirement that each $P(x)$ has a value in the range of [0, 1], and that the sum of all $P(x)$ equal 1. Thus, each cell type is assigned a proportion and the combination of all present cell types does not exceed 100%. The mixtures of cell types A, B, C, and D may be represented as: $E(A)*P(A)+E(B)*P(B)+E(C)*P(C)+E(D)*P(D)$.

The expected value, $E(x)$, may be modelled according to any modeling technique, non-limiting examples of which include a linear regression, logistic regression, resampling methods, subset selection, ridge regression, dimension reduction, non-linear models, tree/forest models, support vector machines, neural networks, or other machine learning algorithms (MLA). In some embodiments, a modeling approach may involve using clustering techniques, non-negative matrix factorization (NMF), grade of membership (GoM), regression techniques such as generalized linear models using gamma or Poisson distributions, and optimization techniques such as directed compression/projected gradient descent to generate RNA profiles for cell types from multi-cell or single-cell sequencing information.

FIG. 4 illustrates, in a graph 430, an example of fitting a gamma distribution to gene expression values for a certain gene across a plurality of subjects, in accordance with some embodiments of the present disclosure. In this example, mean gene expression levels (schematically shown as 0, 10, 20, 30, 40, 50, and 60) for a single gene ("Gene 1") are plotted on the x-axis against a frequency of occurrence of these gene expression levels across all (x) patients being considered, on the y-axis. A gamma distribution model may be selected due to its flexibility in representing RNA expression across multiple genes using different shape and mean parameters of the gamma distribution.

In some embodiments, a machine-learning algorithm (MLA), such as, e.g., a neural network (NN) or any other technique, may be trained using a training data set. For an RNA profile, an exemplary training data set may include imaging, pathology, clinical, and/or molecular reports and patient-related information, such as information curated from an Electronic Health Record (EHR) or genetic sequencing reports. Non-limiting examples of MLAs include supervised algorithms that use linear regression, logistic regression, decision trees, classification and regression trees, Naïve Bayes, nearest neighbor clustering; unsupervised algorithms using the Apriori algorithm, means clustering, principal component analysis, random forest, adaptive boosting; and semi-supervised algorithms using generative approach (such as, e.g., a mixture of Gaussian distributions, mixture of multinomial distributions, hidden Markov models), low density separation, graph-based approaches (such as, e.g., mincut, harmonic function, manifold regularization, etc.), heuristic approaches, or support vector machines. In some embodiments, NNs include conditional random fields, convolutional neural networks, attention based neural networks, long short term memory networks, or other neural network models where the training data set includes a plurality of tumor samples, RNA expression data for each sample, and pathology reports covering imaging data for each sample.

In some embodiments, training an optimization model may include providing datasets including annotated pathology features acquired from imaging data (such as, e.g., cell counts for types of tissue identified in a pathology slide), as well as information on clinical, molecular, and/or genetic characteristics of patients. An MLA can be trained to identify distinct cell-type RNA profiles and also patterns in the outcomes of patients based on their treatments as well as their clinical and genetic information, as they relate to cell-type RNA profiles for various tissues, including tumor tissue.

Figure 5:
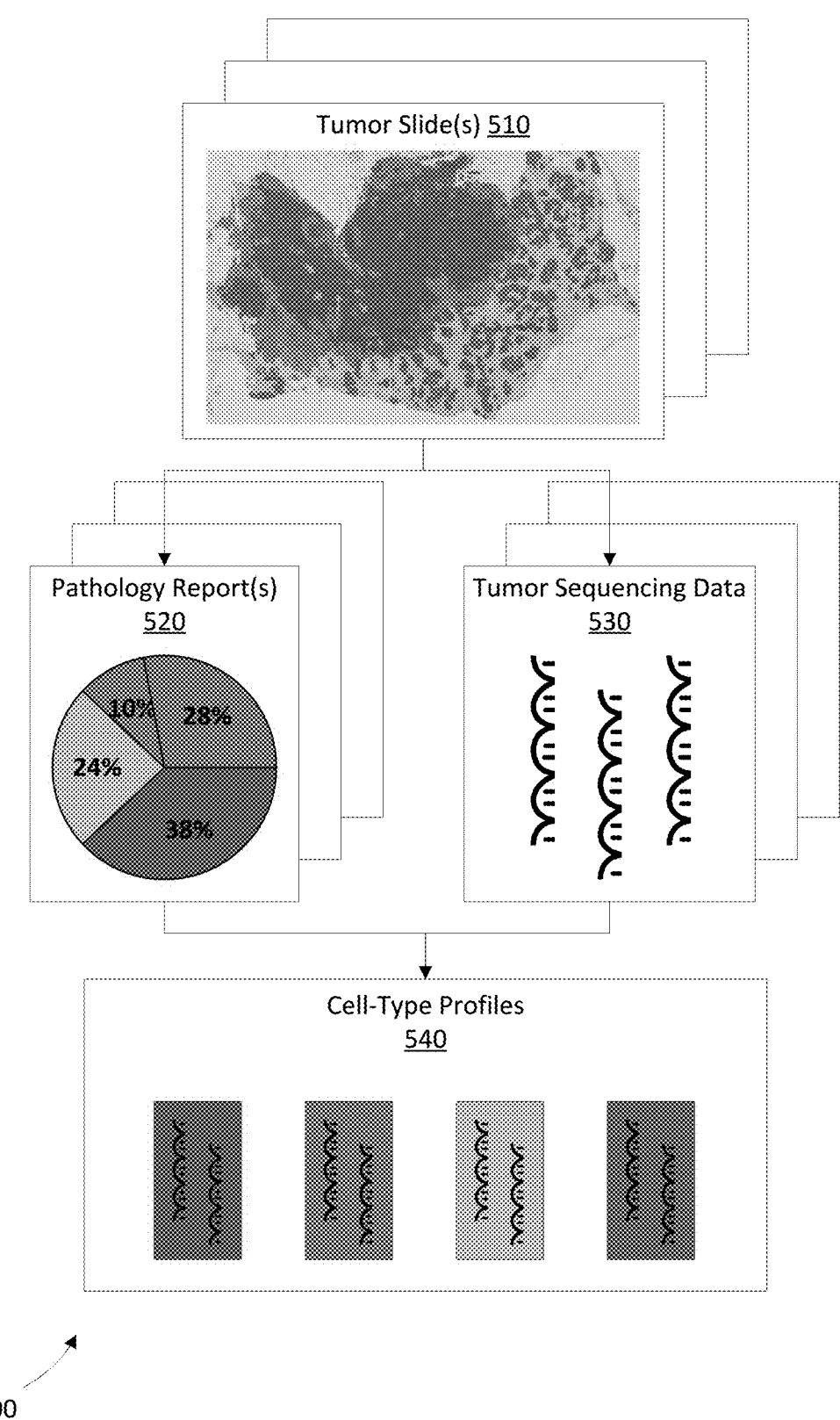
FIG. 5 is a diagram illustrating an example of generating cell-type RNA profiles, in accordance with some embodiments of the present disclosure.

FIG. 5 illustrates an overview 500 of inputs for an optimization model training and model outputs for an exemplary machine learning algorithm used to identify and classify cell-type RNA profiles. As shown in FIG. 5, a plurality of pathology slides 510, such as, e.g., tumor tissue slides (which may or may not include tumor cells) can be acquired and used to generate tumor sequencing data 530 and respective pathology reports 520 (percentages are shown for illustration purposes and are not discussed herein). The MLA model may be trained to identify cell-type RNA profiles using the tumor sequencing data 530 and information in the pathology reports 520.

A suitable training data set may be used for training an optimization model in accordance with embodiments of the present disclosure. In some embodiments, curation of a training data set may involve collecting a series of pathology reports and associated sequencing information from a plurality of patients. For example, a physician may perform a tumor biopsy of a patient by removing a small amount of tumor tissue/specimen from the patient and sending this specimen to a laboratory. The lab may prepare slides from the specimen using slide preparation techniques such as freezing the specimen and slicing layers, setting the specimen in paraffin and slicing layers, smearing the specimen on a slide, or other methods known to those of ordinary skill. For purposes of the following disclosure, a slide and a slice may be used interchangeably. A slide stores a slice of tissue from the specimen and receives a label identifying the specimen from which the slice was extracted and the sequence number of the slice from the specimen. Traditionally, a pathology slide may be prepared by staining the specimen to reveal cellular characteristics (such as cell nuclei, lymphocytes, stroma, epithelium, or other cells in whole or part). The pathology slide selected for staining is traditionally the terminal slide of the specimen block. Specimen slicing proceeds with a series of initial slides that may be prepared for staining and diagnostic purposes. A series of the next sequential slices may be used for sequencing, and then final, terminal slides may be processed for additional staining. In a case when the terminal, stained slide is too far removed from the sequenced slides, another slide may be stained which is closer to the sequenced slides such that sequencing slides are broken up by staining slides. While there are slight deviations from slice to slice, the deviation is expected to be minimal as the tissue is sliced at thicknesses approaching 4 um for paraffin slides and 35 um for frozen slides. Laboratories generally confirm that the distance, usually less than 40 um (approximately 10 slides/slices), has not produced a substantial deviation in the tissue slices.

In (less frequent) cases where slices of the specimen vary greatly from slice to slice, outliers may be discarded and not further processed. The pathology slides 510 may be varying stained slides taken from tumor samples from patients. Some slides and sequencing data may be taken from the same specimen to ensure data robustness, while other slides and sequencing data may be taken from respective unique specimens. The larger the number of tumor samples in the dataset, the more accuracy can be expected from the predictions of cell-type RNA profiles. In some embodiments, a stained tumor slide may be reviewed by a pathologist for identification of cellular features, such as the quantity of cells and their differences from the normal cells of that or similar type.

A pathology report may include various types of information. In some embodiments, the report may include results of pathologist's observations of a tissue sample using the naked eye. In some embodiments, the report may include a size, weight, color and/or other distinguishing features of the tissue sample. In some embodiments, the report includes a description of attributes of the cells of the tissue sample, as the cells appear under a microscope. Non-limiting examples of the attributes may include cell structure, tumor margins, vascular invasion, depth of invasion and pathologic stage. In some embodiments, a clinical stage is determined from the pathologic stage as well as other diagnostic tests such as, for example, X-rays.

Analysis of a cell structure (e.g., in a tumor sample) may include assignment of a histologic grade to a tumor. The histologic grade can be defined as a description of a tumor based on how abnormal the cancer cells and tissue look under a microscope and how quickly the cancer cells are likely to grow and spread. Different grading systems may be used for different types of cancer. The histologic grade helps identify the type of tumor. The grade may be described numerically using, for example, the Scarff-Bloom-Richardson system or a modification thereof. For example, for breast cancer, the Nottingham grading system (also called the Elston-Ellis modification of the Scarff-Bloom-Richardson grading system) is frequently used. A tumor grade can relate to tumor differentiation—for instance, a tumor can be characterised as well-differentiated (or grade 1—the cells of the tumor and the organization of the tumor's tissue are close to those of normal cells and tissue, and the tumor does not grow and spread rapidly rapidly), moderately-differentiated (or grade 2-cells appear slightly different than normal), or poorly differentiated (or grade 3-cells appear abnormal, may lack normal tissue structures, and tend to grow and spread more aggressively than well-differentiated tumors).

Tumor margins may be described as "positive" or "involved" if cancerous cells are present at the edges of the sample tissue. If the cancerous cells are not present at the edges of the tissue, then the margins may be described as "clear," "negative" or "not involved." Vascular or lymphatic system invasion happens when cancer cells break into the blood vessels or lymph channels. A pathologic stage attribute describes the extent of the tumor as determined from the pathology report only. The staging system most often used by pathologists is based on the American Joint Commission on Cancer's (AJCC) TMN (tumor, metastasis, node invasion) system.

In some embodiments, the pathology report may include the following information: patient information (e.g., a name, birth date, and biopsy date), gross description (e.g., color, weight, and size of tissue as seen by the naked eye, microscopic description (e.g., how the sample looks under the microscope and how it compares to normal cells), diagnosis (e.g., a type of tumor/cancer and grade), tumor size, tumor margins (e.g., there may be three findings when the biopsy sample is the entire tumor: (1) positive margins mean that cancer cells are found at the edge of the material removed, (2) negative, not involved, clear, or free margins mean that no cancer cells are found at the outer edge, or (3) close margins are neither negative nor positive). In some embodiments, after identifying the tissue as cancerous, the pathologist may perform additional tests to get more information about the tumor that cannot be determined by looking at the tissue with routine stains, such as hematoxylin and eosin (also known as H&E), under a microscope. The pathology report may include the results of these tests. For example, the pathology report may include information obtained from immunochemical stains (IHC). IHC uses antibodies to identify specific antigens on the surface of cancer cells. IHC can be used to determine where the cancer started, distinguish among different cancer types (such as, e.g., carcinoma, melanoma, and lymphoma), and help diagnose and classify leukemias and lymphomas. The pathology report may also include results of flow cytometry. Flow cytometry is a method of measuring properties of cells in a sample, including the number of cells, percentage of live cells, cell size and shape, and presence of tumor markers on the cell surface. Flow cytometry can be used in the diagnosis, classification, and management of cancers such as acute leukemia, chronic lymphoproliferative disorders, and non-Hodgkin lymphoma. The pathology report may also include results of molecular diagnostic and cytogenetic studies. Such studies investigate the presence or absence of malignant cells, and genetic or molecular abnormalities in specimens.

In some embodiments, proportions of cell types visible in the tumor slides 510, as reported in the pathology reports 520, are used for model training in conjunction with a training data set comprising results of the tumor sequencing-tumor sequencing data 530—to generate cell-type profiles 540. One or more cell-type profiles may be generated for each of the cell types included in the specimen samples (such as, for example, tumor, stroma, lymphocytes, epithelium, healthy tissues, or other cell types).

It should be appreciated that, while the example of FIG. 5 illustrates tumor samples, in some embodiments, samples are acquired from every cell type that may be present in a tumor slide. For example, if a tumor slide additionally includes stroma, epithelium, and lymphocytes, then a trained model (which has been trained with information from pathology reports on quantities of stroma, epithelium, and lymphocyte cells in each of a plurality of training slides) may estimate a number of groupings for each of the stroma, epithelium, and lymphocytes in addition to the classifications of tumor. These groupings may be discerned from lymphoma-targeted specimens, stroma-targeted specimens, or epithelium-targeted specimens. By discerning an accurate number and type of RNA profiles in cell types, effects of noise and/or bias in single-cell and bulk-cell sequencing may be accounted for and eliminated.

Figure 6:
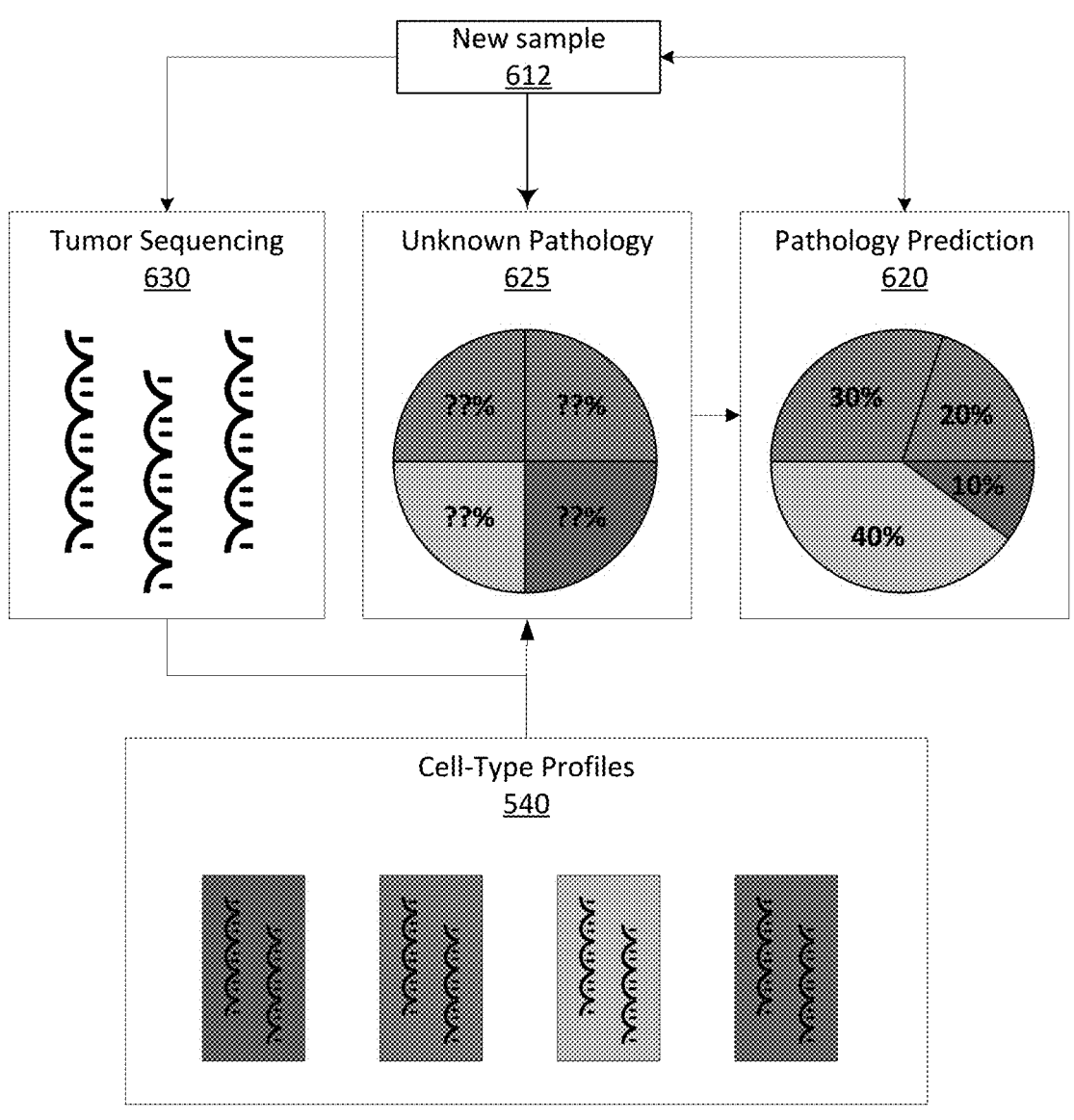
FIG. 6 is a diagram illustrating an example of application the cell-type RNA profiles of FIG. 5 to identify cell types and their proportions in a biological sample, in accordance with some embodiments of the present disclosure.

FIG. 6 illustrates schematically an application of cell-type RNA profiles (e.g., in the form of a trained model) for identification of cell-types and proportions present in a new (test) sample. In some cases, origin(s) of each cell-type in a sample may not be discerned from a pathology report. For example, in a metastatic patient where the tumor's origin is unknown, a pathologist may be able to identify (predict) proportions of cell-types, but not the origin and type of the tumor tissue. As another example, a number of pathology slides acquired from a patient may be sufficient to adequately sequence data obtained from the slides, but not sufficient for staining and therefore assessing proportions of cell types in the sample using imaging data. As another example, a stained slide may not adequately represent a cell-type distribution of the sequenced slides, or the overall tumor purity of the sequenced slides may be unknown. Furthermore, multiple distinct cell-type profiles may exist for tumors of each organ, different immune cells may present at the tumor site, and other tissue(s) (e.g., stroma and epithelium) may be present in a tumor slide. While a pathology report may be used to determine a quantity of cell types which are tumor, stroma, epithelium, and lymphocytes, the report may not include information on a difference between cell types within each classification that presents a distinct RNA profile.

Application of cell-type RNA profiles (e.g., cell-type RNA profiles 540 of FIG. 5) in accordance with embodiments of the present disclosure may overcome the above challenges. For example, as shown schematically in FIG. 6, a composition (e.g., cancer composition) of a new sample 612 may be determined using the techniques in accordance with embodiments of the present disclosure. The new sample 612 (denoted as "new" solely to indicate that its composition is to be determined), which may be processed into a tumor slide (e.g., tumor slide 510 in FIG. 5), may be used to obtain tumor sequencing data 630. In this example, as shown schematically in FIG. 6, an unknown pathology 625 may be associated with the sample 612. Cell-type RNA profiles, e.g., in the form of a respective model, can be applied to the tumor sequencing data 630 and used to identify cell types and their respective proportions, as shown by a "Pathology Prediction" diagram 620 in FIG. 6.

FIG. 7 illustrates by way of example an approach for identifying cell types from a sample comprising a pathology slide, in accordance with some embodiments of the present disclosure. A plurality of cell-type profiles 740 may include groups such as tumor cell-type profiles 702, lymphocyte cell-type profiles 704, stroma cell-type profiles 706, and epithelium cell-type profiles 708. The plurality of cell-type profiles 740 can also include fat cell cell-type profiles, muscle cell-type profiles, and any other cell types. Similarly, healthy tissue may be classified according to tissue site, such as, e.g., breast, lung, brain, colon, prostate, etc. Furthermore, the cell-type profiles 740 may include cell-type profiles specific for a certain tissue and an organ, for example, cell-type profiles for epithelium of the breast, ductal of the breast, lymphocytes of the colon, mucosa of the colon, and other cell histological groupings. In some embodiments, the cell-type profiles 740 may include cell-type profiles classified by the tumor tissue which they surround, such as, e.g., cell-type profiles for stroma of lung tumor or stroma of a first cell type of lung tumor.

As further shown in FIG. 7, a slide obtained from a biological sample from a patient can be represented as a slide profile 750 that may be modeled as a sum of cell types, for example, a sum of the tumor cell types, lymphocyte cell types, stromal cell types, and epithelial cell types. Additional cell types such as, e.g., cell types for healthy tissue and other cell types, may also be included in the slide profile 750, as embodiments are not limited in this respect. Tumor cell types may be further represented by a tumor profile, such as a tumor profile 760. The tumor profile 760 may be modeled as a sum of expected values of all cell type multiplied by a respective percentage value of that cell type. For example, tumor cell types 722 may further be classified into a tumor cell-type 21 724, a tumor cell type 22 726, tumor cell-type 23 728, and tumor cell-type 2 730. As also shown in FIG. 7, sequencing information having tumor cell types 722, 724, 726, 728, and 730 may be expressed by $E(A)*P(\lambda_1)+E(22)*P(\lambda_2)+E(23)*P(\lambda_3)+E(\lambda_4)*P(\lambda_4)$, where $E(x)$ is an expected value of x and $P(x)$ is the proportion of x, and an expected value of x is the cell-type RNA profile of x and a proportion of x is the observed proportion of x in the whole. The cell-type RNA profile, such as cell-type RNA profiles 722, 724, 726, 728, 730, 734, 736, and 738 (illustrated by way of example only) may be stored as a row in cell-type profile matrix 770. Cell-type profile matrix 770 may represent genes in columns and cell types in rows, where each entry stores an associated RNA expression value for the corresponding cell type and gene. It should be appreciated that the cell-type profile matrix 770 is shown in FIG. 7 by way of example only (and shown ways are only examples) and that this matrix may include a large number of rows each representing a respective cell-type profile.

FIG. 8 illustrates an embodiment of a process 800 of generating cell-type RNA expression profiles for each of a plurality of cell types. The process 800 may be implemented, for example, in computer system 300 (FIG. 3) or in another computer system. At block 802, biological samples are obtained from a plurality of subjects, also referred to herein as patients. In some embodiments, as discussed above, a biological sample can be a specimen disposed on a pathology slide. A biological sample can be any other type of a sample. For example, it can be blood, whole blood, plasma, serum, urine, cerebrospinal fluid, fecal, saliva, sweat, tears, pleural fluid, pericardial fluid, or peritoneal fluid samples from the respective subject, any combination thereof, or any other bodily fluid that can be obtained from any type of sample.

At block 804, a plurality of genetic targets can be obtained based on RNA sequencing of the respective biological samples (e.g., tumor specimens) of each respective subject across the plurality of subjects. In this example, the plurality of genetic targets are a plurality of genes, and gene expression data is obtained for each gene and each patient. To obtain the gene expression data (i.e., gene expression level), the total abundance of each gene in each of the samples can be obtained. In some embodiments, gene expression is in the form of RNA abundance, which is interchangeably referred to herein as RNA expression levels.

In some embodiments, the gene expression data, obtained for a gene from each individual sample obtained from a respective patient, may be processed. For example, the gene expression data can be normalized. For example, in some embodiments, information on the genes may be scaled such that their means are equal to one. As another example, additionally, information on the genes having an abundance level below a certain threshold and genes with expression data not following a certain statistical distribution (e.g., a gamma distribution, in this example) can be removed from further analysis. Also, genes that may not contribute to a difference between various cell types may not be used in analysis.

In some embodiments, the gene expression data is processed by normalization across multiple DNA/RNA sequencing pipelines. For example, a sequencing pipeline may utilize Kallisto, Salmon, STAR, RSEM, Sailfish, eXpress, or other various RNA quantifiers. Results from each quantifier may have certain biases in the RNA expression results. Normalization may be applied to each respective dataset to remove effects of a bias introduced by a respective quantifier. For example, if a first quantifier results in a greater expression of certain transcripts or RNA expressions, a normalization may reduce the expression values for those transcripts or RNA expressions to ensure the dataset is balanced according to all integrated sequencing pipelines. Additional normalization may be applied to filter out genes with expression levels below a certain threshold, across all patients. In this way, only genes which are relevant to classification of cell types may be processed.

At block 806, a predicted proportion of cell types is obtained for each patient's sample, e.g., in the form of cell-type proportion dataset(s). As discussed above, in various embodiments of the present disclosure, the predicted proportion can be obtained from an imaging analysis (automatic and/or manual) of a pathology slide or another type of a specimen. For example, the predicted proportions of cell types in a sample can be obtained from a pathologist report, data generated by a flow cytometer, or another cell-count analyzer. The proportions of cell types in the sample are predicted such that the sum of the proportions equals to 1. The prediction can also involve predicting a number of unknown cell types for each patient. For example, if the proportions of the predicted (estimated) cell types do not sum up to one (or to 100% if percentages are used), it may be determined that the sample includes unknown cell types.

The predicted cell type proportions may include predicted proportions for cancer cell types and non-cancer cell types. For example, as discussed above, predicted proportions can be for a tumor cell type (which can include tumor subtypes), lymphocytes cell type, stroma cell type, and epithelium cell type.

It should be noted that the gene expression data obtained from more than one sample from the same patient. For instance, multiple pathology slides can be obtained from a patient (e.g., gene expression data can be obtained from one slide and imaging data can be obtained from another slide, prepared from a specimen taken in close proximity to the slide from which the gene expression data is obtained). For the purpose of the analysis of the sample composition in accordance with this embodiment, such multiple samples obtained from the patient may be taken as a single sample, and the proportions of cell types estimated to be present in that sample are predicted such that they sum to 1.

At block 808 of the process 800, one or more unknown cell types are obtained. The number of unknown cell types may vary based upon a desired specificity of the classification. For example, cell types such as lymphocytes, stroma, epithelium, and healthy tissue may be generalized to a single cell type, by identifying a single RNA expression profile that matches all of the different types of cells that may be categorized as lymphocytes, stroma, epithelium, and healthy tissue, respectively. This may be performed by identifying common factors that are present in each of the respective cell types. In some embodiments, while the lymphocytes, stroma, epithelium, and healthy tissue may be generalized to a single cell type, tumor tissue may be categorized into k cell-types which may be identified using various techniques including one or more of a clustering algorithm (e.g., provided by CountClust or any other package), a grade of membership model, etc.

In some embodiments, a cross validation or any other approach can be used for model training and evaluation. For example, in cross validation, a number of cell types, $k_i$, may be iteratively evaluated over a range of k to identify the most probable number of cell types. The number of unknown cell types may also include categorizing each of the different types of cells individually, such that lymphocytes may have $k_1$ cell types, stroma may have $k_2$ cell types, epithelium may have $k_3$ cell types, healthy tissues may have $k_4$ cell types, and tumor tissues may have $k_5$ cell types, where the number of cell types may be a summation of the $k_{1-5}$ cell types. Cell types which RNA expression profiles are already known are not included in the number of unknown cell types.

In some embodiments, the number of unknown cell types can additionally or alternatively be obtained, at block 808 of FIG. 8, based on analysis of imaging data acquired from samples. The number of known cell types can be predicted automatically and/or manually. The number of unknown cell types may be received along with the gene expression data and cell-type proportion data.

At block 810, initial estimates of proportions may be assigned to unknown cell types calculated at block 808. A gamma distribution can be fitted to the gene expression data at block 812. As discussed above, in some embodiments, the gamma distribution is initialized with shape and mean parameters. The mean can be an average mean across all patients for each gene.

The processing at blocks 810 and 812 can be performed in any order or at least partially simultaneously, as shown in FIG. 8 (811). In some implementations, the processing at blocks 810 and 812 can be performed in parallel.

In embodiments of the present disclosure, the sum of proportions of cell types represents the whole and equals to 100%. As an example, predicted proportions for cell types (determined at block 806 of FIG. 8, as discussed above) can be $k_1$=40% tumor, $k_2$=30% epithelium, $k_3$=20% stroma, and $k_4$=10% lymphocytes. Similarly, a sum of proportions of unknown cell types that make up each category (e.g., tumor, epithelium, stroma, and lymphocytes) is modeled as being equivalent to the entirety of the cell types. For example, if it is known that 40% of the sample is 7 unknown cell types, in some embodiments, 7 random values may be generated and scaled up such that their sum equals to 40%. An example of an approach to accomplish this may be to randomly generate k values, such as the k values from the summation of the cell types. By summing each of the randomly generated values of each k and dividing by the sum (of those random values), the random values will represent a random proportion of the 100% and, by multiplying each randomly generated k value with the respective previously determined k values, the respective portions may be scaled to the correct proportion. As an illustration, for unknown tumors having a $k_1$=10 at 40%, epithelium having a $k_2$=5 at 30%, stroma having a $k_3$=2 at 20%, and lymphocytes having $k_4$=7 at 10%, the proportions for tumors may be calculated by randomly generating 10 values, summing the 10 values, dividing each value by the summation, and then multiplying by 0.4 to scale the random numbers to add up to 40%. If the ten values are (2, 4, 6, 8, 10, 12, 14, 16, 18, 20), a summation of all 10 values is 110, dividing each value by 110 and multiplying by .4 results in (0.007272727, 0.014545455, 0.021818182, 0.029090909, 0.036363636, 0.043636364, 0.050909091, 0.058181818, 0.065454545, 0.072727273) which sum to .4 or 40%. These steps may be performed for each of the unknown cell types to generate initial guesses for the proportions. In some cases, if a respective $k_n$ is 0, or there are no unknown cell types, a random probability will not be generated for that $k_n$.

Referring back to FIG. 8, at block 812, the initial estimates for a gamma distribution may be fit to the gene expression data, using the proportions assigned to the unknown cell types (block 810) and the obtained predicted proportions of known cell types (block 806). In some embodiments, the initial estimate fitting (e.g., a best fit estimate) may be performed across all genes at once or it may be performed on a gene-by-gene basis. As schematically shown in FIG. 8 (block 811), the processing at blocks 810 and 812 may be performed as part of the same process. As a result of the processing at block 811, each gene in the plurality of genes is associated with the shape and mean parameters, and the proportions are assigned to cell types.

In some embodiments, known cell-type RNA expression profiles may be used in the processing in this example, e.g., by pre-populating a cell types by gene matrix with the respective gene expression values for the known cell types. For example, if lymphocytes have four previously identified cell types, the four columns of the cell-type matrix for lymphocytes may be pre-populated with the respective RNA cell-profiles. Cross validation may be performed to test for a likelihood of other, unknown lymphocyte cell-types, and a respective k value may be set to generate an initial estimate of the unknown cell-types. When both known and unknown cell types exist for a respective cell type, the probabilities can be shared among both the known and unknown cell types. For example, if four lymphocyte cell-type RNA profiles are known and cross validation reveals that another two cell types may exist, then a k of 6 is input to the algorithm but, given that the four of the six columns of the cell-type RNA profile matrix are pre-populated, cell-type RNA profiles for the known four may not be recalculated.

At block 814 of FIG. 8, the mean parameter of the gamma distribution is iteratively updated across the plurality of genes, while the shapes for the cell types, proportions of the cell types (observed and unknown) and the initial values for the gamma distribution are held constant. At block 816, the shape parameter of the gamma distribution is iteratively updated, while the means for the cell types, proportions of the cell types (observed and unknown) and the initial values for the gamma distribution are held constant. At block 818, the proportions of the cell types for each patient are iteratively updated, with the mean and shape parameter of the gamma distributions being constant. It is assumed that each patient has that patient's own proportions of cell types, but the plurality of patients share the shape and the mean parameters.

The proportions may be calculated for each patient by weighing the contributions of each gamma distribution for each gene across all genes. A best fit may be identified by applying projected gradient descent to estimate percentage changes across the unknown cell types until convergence. For example, in embodiment, convergence for proportions may be met when the absolute mean difference of proportions from each iteration of projected gradient descent is below a certain threshold value.

As shown in FIG. 8, the processing at blocks 814, 816, and 818 can be performed as part of the same process (block 815) and may be processed in parallel, serially, or a combination thereof. In some embodiments, the fit updates (iterative updating of parameters until convergence to a desired value or a value within a desired range of values) at block 815 are performed by a projected gradient descent algorithm for the gamma distribution-based model of gene expression. In some embodiments, a maximum likelihood (ML) estimation, which can be an ML-based minimum mean squared error (MMSE) estimate may be used in fitting the gamma distribution to the gene expression data.

The processing at block 815 may generate a cell-type profile for each cell type in a plurality of cell types, as shown in FIG. 8. In some implementations, the generated cell-type profiles may be stored in a cell-type RNA profile matrix. For example, the cell-type RNA profile matrix may have a number of columns equal to the number of cell-types and a number of rows equal to the number of genes. The number of genes may be all known genes, a subset of genes which are identified as latent factor genes, such as, e.g., genes that distinguish between cell types during clustering, or a subset of genes defined by an input cell-type RNA profile matrix, which can have data on known cell-type RNA expression profiles. In this way, the process 800 may result in the plurality of cell-type profiles determined for respective cell types, and the respective model is trained to recognize the cell-type RNA profiles. As also shown in FIG. 8, the process 800 generates proportions of the cell types for each of the plurality of patients.

Figure 9:
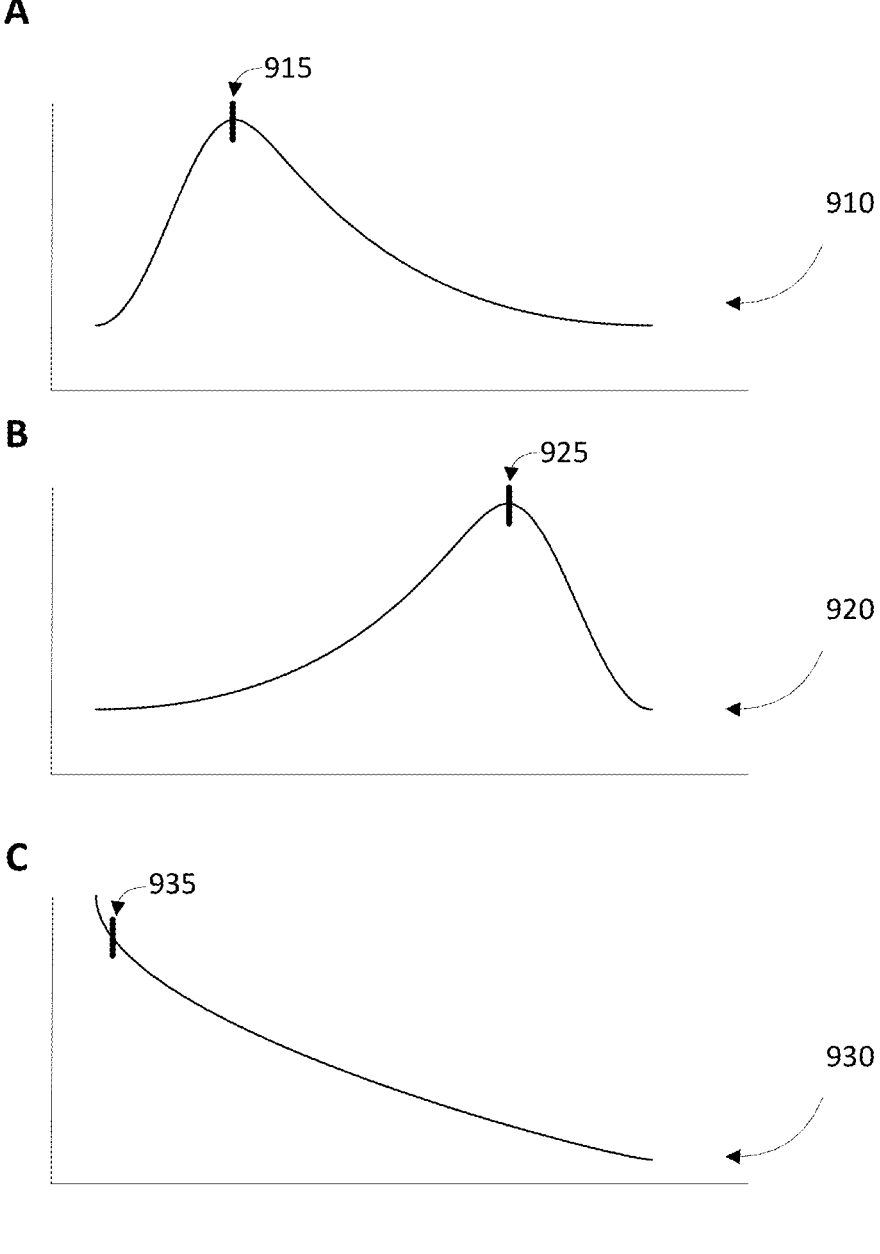
FIG. 9 is a diagram illustrating three gamma distributions that may be used to model gene expression data, in accordance with some embodiments of the present disclosure.

FIG. 9 is a schematic diagram illustrating examples of gamma distributions 910 (panel A), 920 (panel B), and 930 (panel C), having different shape and mean (915, 925, 935, respectively) parameters.

In some embodiments, gamma distribution-based models (e.g., the model generated and trained as shown in FIG. 8), may be trained for a certain type of tissue or for multiple types of tissues. Performance of models trained for a certain type of tissue (e.g., a first cancerous tissue) may be compared to performance of models trained for another type of tissue (e.g., a second cancerous tissue). For example, a cell type identified in a breast tumor may be similar to a cell type identified in a prostate tumor such that treatments may be recommended based on this similarity, as discussed in more detail below.

In some embodiments, gamma distribution models for cell-type RNA expression profiles may be generated using data obtained from organoids. It should be appreciated that cell-type RNA expression profiles may be generated using information on known cell types, and that models generated in accordance with embodiments of the present disclosure can be refined (e.g., retrained) as new data becomes available.

FIGS. 10A-10C illustrate a method for determining a cancer composition of a subject, in accordance with some embodiments of the present disclosure. At block 1002 of FIG. 10A, a method for determining a cancer composition of a subject is provided. The method may be implemented at a computer system (e.g., system 300 of FIG. 3) having one or more processors and memory storing one or more programs for execution by the one or more processors. It should be appreciated however that data used by the processors can be stored in any suitable memory.

As shown at block 1004, the method may involve generating, in electronic form, for each respective genetic target in a first plurality of genetic targets, a corresponding shape parameter, which can be done based at least in part on RNA sequencing of one or more respective biological samples obtained from a respective tumor specimen of each respective subject across a plurality of subjects. The genetic targets may be various genetic targets, as embodiments of the present disclosure are not limited in this respect. For example, in some embodiments, the first plurality of genetic targets are a first plurality of genes (block 1006). In some embodiments, the first plurality of genetic targets are a transcriptome (block 1008). As another example, each genetic target in the first plurality of genetic targets may be a different independent RNA for a corresponding gene in a plurality of genes, as shown at block 1010. As yet another example, the first plurality of genetic targets may be a first plurality of genetic loci, as shown at block 1012. In some cases, the first plurality of genetic targets are selected from 20,000 different human genes or 128,000 different human RNA transcripts, though the genetic targets may comprise any other number of genes. A panel including virus and/or bacterial genomes may further include cell-type RNA expression profiles for any included respective virus or bacterial genes.

The biological samples may be samples of any of various types. For example, in some embodiments, the biological samples are one or more pathology tissue slides (block 1014). In some embodiments, the one or more respective biological samples are one or more blood, whole blood, plasma, serum, urine, cerebrospinal fluid, fecal, saliva, sweat, tears, pleural fluid, pericardial fluid, or peritoneal fluid samples from the respective subject, or any combination thereof. The plurality of subjects may comprise any number of subjects, e.g., fewer than 100 subjects, 100 subjects, more than 100 subjects, or more than 10,000 subjects.

The pathology tissue slides may comprise, for example, between 5 and 20 pathology tissue slides. In some embodiments, each pathology tissue slide in the one or more pathology tissue slides is between 4 and 5 microns thick. However, it should be appreciated that embodiments are not limited in this respect.

The method for determining the cancer composition of the subject further comprises, as shown at block 1016, obtain, in electronic form, for each respective subject across the plurality of subjects, a corresponding relative proportion of one or more sets of cell types in a plurality of sets of cell types. The relative proportions may be, for example, predicted proportion of cell type 1-1 (322-1-1) or predicted proportion of cell type N-1 (322-N-1), shown in FIG. 3. The obtaining step 1016 may generate proportions randomly or it may obtain them from measured data (e.g., gene expression data and/or any other type(s) of data) for the subject.

It should be noted that the proportionality knowledge across all sets of cell types may not be available for each cell type. Also, in some cases, no knowledge may be available. The relative proportions may be assigned randomly. Accordingly, at shown at block 1018, in some embodiments, the corresponding relative proportion of one or more sets of cell types in the plurality of sets of cell types comprises initializing the relative proportion of one or more sets of cell types in the plurality of sets of cell types to random proportions.

Furthermore, in some embodiments, proportions of one or more cell types present in the sample may not be known. Thus, in such embodiments, as shown at block 1020, the proportions may be obtained for less than the entirety of the plurality of sets of cell types.

As discussed above, in various embodiments, the relative proportions may be provided based on a pathology report generated for the sample, or using any other information. Thus, as shown at block 1022 of FIG. 10A, the relative proportion of the one or more sets of cell types in the plurality of sets of cell types for a corresponding subject may originate from a pathology report for the corresponding subject, as shown at block 1022.

Further, as shown at block 1024 of FIG. 10B, the method for determining the cancer composition of the subject further comprises obtaining, in electronic form, for each respective subject across the plurality of subjects, for each respective genetic target in the first plurality of genetic targets, a corresponding measure of central tendency of an abundance of the respective genetic target. In some embodiments, the corresponding measure of central tendency of an abundance such as, e.g., a mean parameter of a gamma distribution for a certain gene, can be obtained (e.g., initiated) based on, at least in part, on the RNA sequencing of one or more respective biological samples obtained from the respective tumor specimen of each respective subject across the plurality of subjects. For example, as discussed above, the mean parameter of the gamma distribution for a certain gene can be initialized as an average mean value of expression of that gene across all patients.

The corresponding measure of central tendency of the respective genetic target may be an arithmetic mean, weighted mean, midrange, midhinge, trimean, Winsorized mean, mean, or mode of RNA sequence reads measured for the respective genetic target in the one or more biological samples obtained from the respective subject (block 1026).

In some embodiments, one or both the shape and mean parameters may be obtained at least in part based on RNA sequencing of the one or more respective biological samples.

In some embodiments, as shown at block 1028, the corresponding shape parameter and the corresponding measure of central tendency of an abundance for a genetic target in the first plurality of genetic targets defines a mean and shape of a gamma distribution, a mean and variance of a normal distribution, a means of a Poisson distribution, or counts and probabilities of a binomial distribution for the genetic target. In some embodiments (block 1030), the corresponding relative proportion of one or more sets of cell types in a plurality of sets of cell types for a respective subject is obtained from a pathologist or by flow cytometry.

A cell type in a set of cell types may be a cell type of any type. For example, the cell type may be a tumor cell type, a healthy cell type, an immune cell type, a lymphocyte cell type, a stroma cell type, an epithelial cell type, or any combinations thereof. In other embodiments, a viral or bacterial cell type may also be calculated. In some embodiments, the plurality of calculated cell types in the first set of cell types comprises tumor subtypes 1-N, healthy tissue subtypes 1-M, lymphocyte subtypes 1-X, stroma subtypes 1-Y, and epithelial subtypes 1-Z, wherein N, M, X, Y, and Z are all positive integers.

At block 1032 of FIG. 10B, the method described in this example further includes refining the first optimization model subject to a first plurality of constraints. The first plurality of constraints include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects, the refining thereby identifying a plurality of calculated cell types in a first set of cell types in the plurality of sets of cell types, the refining further generating a respective calculated cell type RNA expression profile for each calculated cell type in the plurality of calculated cell types.

The refining may be performed in various ways. In some embodiments, the refining may use a k-fold cross validation of the plurality of subjects, subject to the first plurality of constraints, to identify the number of calculated cell types in the plurality of calculated cell types.

In some embodiments, the first set of cell types is cancer and each remaining set of cell types is non-cancer. In some embodiments, the first set of cell types is cancer and the plurality of sets of cell types further comprise a second set of cell types that comprises one or more reference cell types for stroma cells, a third set of cell types that comprises one or more reference cell types for epithelium cells, and a fourth set of cell types that comprises one or more reference cell types for lymphocytes. Additionally, in some cases, the plurality of sets of cell types further comprise a fifth set of cell types that is healthy cells, a sixth set of 'cell' types that is viral, and/or a seventh set of cell types that is bacterial.

In some embodiments, the method further comprises obtaining, independent of each respective tumor specimen, for each respective reference cell type represented in the second, third and fourth set of cell types, a corresponding reference cell type RNA expression profile that comprises a corresponding third plurality of genetic targets, thereby obtaining a plurality of reference cell-type RNA expression profiles. The first plurality of constraints may further include the plurality of reference cell-type RNA expression profiles.

In some embodiments, the plurality of calculated cell types in the first set of cell types consists of more than two calculated cell types.

In some embodiments, each respective calculated cell-type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters. The corresponding second plurality of genetic targets of a first calculated cell type RNA expression profile for a first calculated cell type in the plurality of calculated cell types may include genes that are not present in the corresponding second plurality of genetic targets of a second calculated cell type RNA expression profile for a second calculated cell type in the plurality of calculated cell types.

In some embodiments, each respective calculated cell-type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters. The corresponding second plurality of genetic targets of a first calculated cell type RNA expression profile for a first calculated cell type in the plurality of calculated cell types may comprise between one hundred and one thousand genes.

In some embodiments, each respective calculated cell type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters. In some embodiments, the corresponding second plurality of genetic targets of a first calculated cell type RNA expression profile for a first calculated cell type in the plurality of calculated cell types comprises at least 25, 50, 100, 150, 200, or 250 selected from FIG. 13.

In some embodiments, the plurality of sets of cell types is more than two sets of cell types. The respective tumor specimen may be a tumor from an origin in an enumerated list of origins. In some cases, the enumerated list of origins may be a single origin, non-limiting examples of which include adrenal, biliary tract, bladder, bone/bone marrow, breast, brain, cervix, colon/rectum, esophagus, gastrointestinal, head and neck, hepatobiliary, kidney, liver, lung, ovary, urinary/bladder, ovary, pancreas, pelvis, pleura, prostate, renal, skin, small bowel, stomach, testis, thymus, or thyroid.

In some embodiments, each respective calculated cell type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters. The corresponding second plurality of genetic targets may be a respective calculated cell type RNA expression profile is a subset of the first plurality of genetic targets.

The generation of the cell-type RNA expression profile for each calculated cell type in the plurality of calculated cell types (block 1032 of FIG. 10B) may be performed by training (refining) the first optimization model. Once the optimization model is trained, the process 1000 may proceed to using the respective calculated cell type RNA expression profile for each calculated cell type in the plurality of calculated cell types to determine the cancer composition of the subject, as shown at block 1034 of FIG. 10C. In this way, for example, a composition of a new sample may be identified. It should be noted that a cell-type composition of a patient having a condition or disease other than cancer can be determined using the method in accordance with embodiments of the present disclosure, as the embodiments are not limited to cancer samples.

In some embodiments, as shown at block 1036 of FIG. 10C, the using comprises: obtaining, in electronic form, a test expression set that comprises, for each respective genetic target in the first plurality of genetic targets, a corresponding measure of central tendency of an abundance of the respective genetic target, based at least in part on RNA sequencing of one or more respective biological samples obtained from a tumor specimen of a test subject; obtaining, in electronic form, a test proportion set that comprises the corresponding relative proportion of each set of cell types in the plurality of sets of cell types; and refining a second optimization model subject to a second plurality of constraints. The second plurality of constraints include (i) the test expression set, (ii) the test proportion set, and (iii) the respective calculated cell type RNA expression profile for each calculated cell type in the plurality of calculated cell types, thereby identifying the cancer composition of the test subject in the form of a relative proportion of each calculated cell type in the plurality of calculated cells types.

In some embodiments, each respective calculated cell type RNA expression profile for each calculated cell type in the plurality of calculated cell types comprises a corresponding second plurality of genetic targets and, for each respective genetic target in the corresponding second plurality of genetic targets, a corresponding set of fitted expression distribution parameters in a plurality of fitted expression distribution parameters. In such embodiments, the refining the first optimization model comprises (A) for each respective subject in the plurality of subjects, for each calculated cell type in the plurality of calculated cell types, assigning a respective seed proportion, bounded by a relative proportion of the first set of cell types in the respective subject, to each calculated cell type in the plurality of calculated cell types, thereby obtaining a set of proportions across the plurality of subjects; (B) refining the corresponding set of fitted expression distribution parameters of each respective genetic target in each corresponding second plurality of genetic targets for each respective calculated cell type RNA expression profile in the plurality of calculated cell types using at least (i) the set of proportions across the plurality of subjects, (ii) the corresponding shape parameter for each respective genetic target in the first plurality of genetic targets for each respective subject in the plurality of subjects, (iii) the corresponding measure of central tendency of an abundance of each respective genetic target in the first plurality of genetic targets, for each respective subject across the plurality of subjects, and (iv) the corresponding relative proportion of each set of cell types in the plurality of cell types for each respective subject in the plurality of subjects; and (C) refining the set of proportions across the plurality of subjects using at least (i) the corresponding set of fitted expression distribution parameters of each respective gene in each corresponding second plurality of genes for each respective calculated cell type RNA expression profile in the plurality of calculated cell types (ii) the corresponding shape parameter for each respective genetic target in the first plurality of genetic targets for each respective subject in the plurality of subjects, (iii) the corresponding measure of central tendency of an abundance of each respective genetic target in the first plurality of genetic targets, for each respective subject across the plurality of subjects, and (iv) the corresponding relative proportion of each set of cell types in the plurality of cell types for each respective subject in the plurality of subjects.

In some embodiments, the refining (B) is performed on a genetic target by genetic target and subject by subject basis. In some embodiments, the refining (B) is performed on a genetic target by genetic target basis across the plurality of subjects. In some embodiments, the refining (B) and the refining (C) are iteratively repeated until a first convergence criterion is satisfied. The first convergence criterion may be evaluated in accordance with a first gradient descent algorithm or a first gradient ascent algorithm.

In some implementations, the first set of cell types is cancer and the plurality of sets of cell types further comprises a second set of cell types that comprises one or more reference cell types for stroma cells, a third set of cell types that comprises one or more reference cell types for epithelium cells, and a fourth set of cell types that comprises one or more reference cell types for lymphocytes. The method may further comprise obtaining, independent of the plurality of subjects, for each respective reference cell type represented in the second, third and fourth set of cell types (or including fifth, sixth, and/or seventh 'cell' types), a corresponding reference cell type RNA expression profile that comprises a corresponding third plurality of genetic targets, thereby obtaining a plurality of reference cell type RNA expression profiles. The refining (B) and (C) may further use the plurality of reference cell type RNA expression profiles.

In some embodiments, each respective set of expression distribution parameters in a plurality of sets of expression distribution parameters comprises a corresponding shape parameter k and a corresponding mean parameter u that collectively describe a corresponding gamma distribution of the expression of a corresponding genetic target in the first plurality of genetic targets across the plurality of subjects and wherein the corresponding mean parameter u is a mean of the expression value for the corresponding genetic target across the plurality of subjects, and each respective set of fitted expression distribution parameters of each respective genetic target in the respective second plurality of genetic targets of each respective calculated cell type RNA expression profile for each calculated cell type in the plurality of calculated cell types comprises a corresponding shape parameter k and a corresponding mean parameter u that collectively describe a corresponding gamma distribution of the respective genetic target in the respective calculated cell type RNA expression profile.

In some embodiments, the refining (B) comprises refining the corresponding mean parameter u, while holding the corresponding shape parameter k fixed, for each set of fitted expression distribution parameters of each respective genetic target in each corresponding second plurality of genetic targets for each respective calculated cell type RNA expression profile in the plurality of calculated cell types using at least (i) the set of proportions across the plurality of subjects, (ii) the corresponding set of expression distribution parameters for each respective genetic target in the first plurality of genetic targets for each respective subject in the plurality of subjects, (iii) the corresponding relative proportion of each set of cell types in the plurality of cell types for each respective subject in the plurality of subjects, and (iv) the corresponding shape parameter k for each set of fitted expression distribution parameters of each respective genetic target in each corresponding second plurality of genetic targets for each respective calculated cell type RNA expression profile in the plurality of calculated cell types. The refining (B) can also comprise refining the corresponding shape parameter k, while holding the corresponding mean parameter u fixed, for each set of fitted expression distribution parameters of each respective genetic target in each corresponding second plurality of genetic targets for each respective calculated cell type RNA expression profile in the plurality of calculated cell types using at least (i) the set of proportions across the plurality of subjects, (ii) the corresponding set of expression distribution parameters for each respective genetic target in the first plurality of genetic targets for each respective subject in the plurality of subjects, (iii) the corresponding relative proportion of each set of cell types in the plurality of cell types for each respective subject in the plurality of subjects, and (iv) the corresponding mean parameter u for each set of fitted expression distribution parameters of each respective genetic target in each corresponding second plurality of genetic targets for each respective calculated cell type RNA expression profile in the plurality of calculated cell types.

Furthermore, in some embodiments, the refining steps described above are iteratively performed until a second convergence criterion is satisfied. The second convergence criterion may be evaluated in accordance with a second gradient descent algorithm or a second gradient ascent algorithm.

In some embodiments, a computer system for determining a cancer composition of a subject is provided. The computer system comprises at least one processor, and a memory storing at least one program for execution by the at least one processor. The at least one program comprises instructions for: generating, in electronic form, for each respective genetic target in a first plurality of genetic targets, a corresponding shape parameter, at least in part on RNA sequencing of one or more respective biological samples obtained from a respective tumor specimen of each respective subject across a plurality of subjects; obtaining, in electronic form, for each respective subject across the plurality of subjects, a corresponding relative proportion of one or more sets of cell types in a plurality of sets of cell types; obtaining, in electronic form, for each respective subject across the plurality of subjects, for each respective genetic target in the first plurality of genetic targets, a corresponding measure of central tendency of an abundance of the respective genetic target, based at least in part on RNA sequencing of one or more respective biological samples obtained from the respective tumor specimen of the respective subject; and refining a first optimization model subject to a first plurality of constraints. The first plurality of constraints include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects, the refining thereby identifying a plurality of calculated cell types in a first set of cell types in the plurality of sets of cell types, the refining further generating a respective calculated cell type RNA expression profile for each calculated cell type in the plurality of calculated cell types. The instructions are further for using the respective calculated cell type RNA expression profile for each calculated cell type in the plurality of calculated cell types to determine a cancer composition of a subject.

In some embodiments, a non-transitory computer-readable storage medium is provided that stores thereon program code instructions that, when executed by a processor, cause the processor to perform a method for determining a cancer composition of a subject. The method comprises generating, in electronic form, for each respective genetic target in a first plurality of genetic targets, a corresponding shape parameter, based at least in part on RNA sequencing of one or more respective biological samples obtained from a respective tumor specimen of each respective subject across a plurality of subjects; obtaining, in electronic form, for each respective subject across the plurality of subjects, a corresponding relative proportion of one or more sets of cell types in a plurality of sets of cell types; obtaining, in electronic form, for each respective subject across the plurality of subjects, for each respective genetic target in the first plurality of genetic targets, a corresponding measure of central tendency of an abundance of the respective genetic target, based at least in part on RNA sequencing of one or more respective biological samples obtained from the respective tumor specimen of the respective subject; and refining a first optimization model subject to a first plurality of constraints. The first plurality of constraints include (i) the corresponding shape parameter of each respective genetic target in the first plurality of genetic targets, (ii) the corresponding relative proportion of one or more sets of cell types for each respective subject in the first plurality of subject, and (iii) the corresponding measure of central tendency of an abundance of each respective genetic target in the first plurality of genetic targets, for each respective subject across the plurality of subjects, the refining thereby identifying a plurality of calculated cell types in a first set of cell types in the plurality of sets of cell types, the refining further generating a respective calculated cell type RNA expression profile for each calculated cell type in the plurality of calculated cell types. The method also comprises using the respective calculated cell type RNA expression profile for each calculated cell type in the plurality of calculated cell types to determine a cancer composition of a subject.

In some embodiments, a method for generating cell-type RNA expression profiles is provided that comprises, at a computer system having one or more processors and memory storing one or more programs for execution by the one or more processors: obtaining, in electronic form, for each respective specimen across a plurality of specimens, a corresponding set of expression values based, at least in part, on RNA sequencing obtained from each respective specimen across a plurality of specimens, thereby obtaining a plurality of sets of expression values; obtaining, in electronic form, for each respective specimen in the plurality of specimens, a corresponding relative proportion of at least one set of cell types in a plurality of sets of cell types, wherein the sum of the corresponding relative proportions across the plurality of sets of cell types is 100%; and refining a first optimization model subject to a first plurality of constraints. The first plurality of constraints include (i) a corresponding set of expression distribution parameters; and (ii) the corresponding relative proportion of each set of cell types in the plurality of cell types, thereby identifying a plurality of calculated cell types in a first set of cell types in the plurality of sets of cell types, the refining further generating a respective calculated cell type RNA expression profile for each calculated cell type in the plurality of calculated cell types. The method also comprises using the respective calculated cell type RNA expression profile for each calculated cell type in the plurality of cell types to determine a cancer composition of a specimen.

The techniques described in embodiments of the present disclosure may be used in various clinical applications, by providing insights on cell types present in biological samples, and utilizing those insights for diagnosing and therapeutic purposes.

Figure 11:
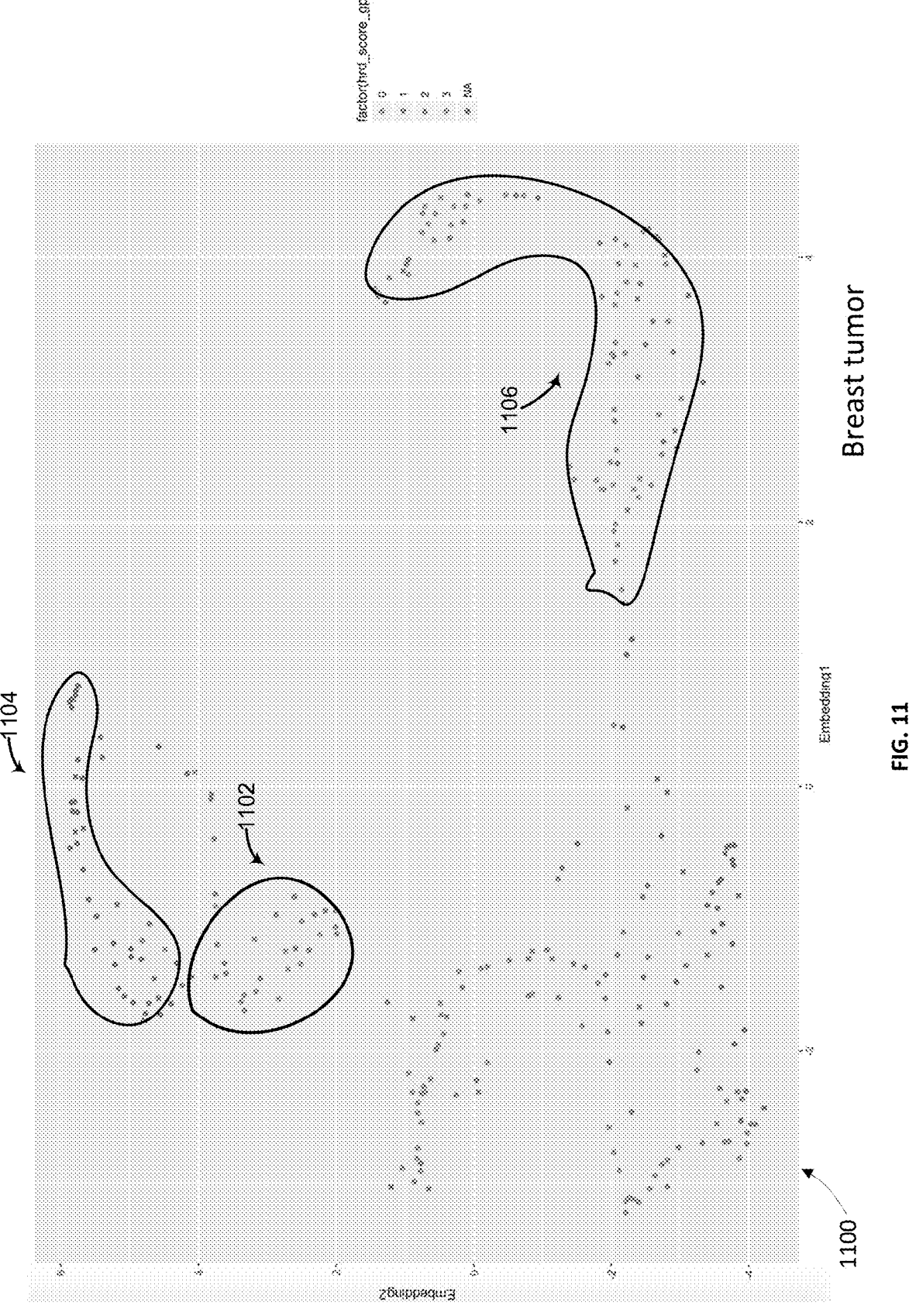
FIG. 11 is a plot of breast and prostate tumor cell types according to similarity and latent factors, in accordance with some embodiments of the present disclosure.

FIG. 11 illustrates an example of results of application of a gamma distribution model trained for breast cancer tumors and prostate cancer tumors. By applying a gamma distribution model, the systems and methods are able to remove the RNA expression of the non-tumor cells in each tumor specimen from the RNA expression of the tumor cells in each tumor specimen. As a result, the remaining RNA expression reflects the expression of the tumor cells in each breast cancer specimen and prostate cancer specimen. FIG. 11 illustrates a comparison of such remaining RNA expression for each specimen plotted in the figure. In this example, results for prostate tumors and breast tumors (with the dimensions reduced from 7 to 2) are plotted on plot 1100, with each dimension corresponding to latent factors. For example, the x-axis may be a latent factor relating to the likelihood of a breast tumor being estrogen receptor negative (ER-) or positive (ER+), and the y-axis may be a latent factor relating to a tumor tissue similarity metric. Prostate tumors are shown clumping together at about Y=6 and about Y=4 regions (see clusters 1102, 1104), and breast tumors are shown clumping together at about X=2 and about X=4 (see cluster 1106) according to ER+ and ER-sub-types, respectively, while some similarities are shown as some ER+breast tumor cell-types cluster close to the prostate cell-types at Y=6 while other prostate cells are clustering close to ER+breast cell types at Y=4. Due to the similarity in cell-types between the breast and prostate tumor cell-types, a treating physician may recommend a patient having a prostate tumor clustering with ER+breast tumor cell-types begin a treatment regimen that is particular effective for the ER+breast tumor cell-types.

Figure 12:
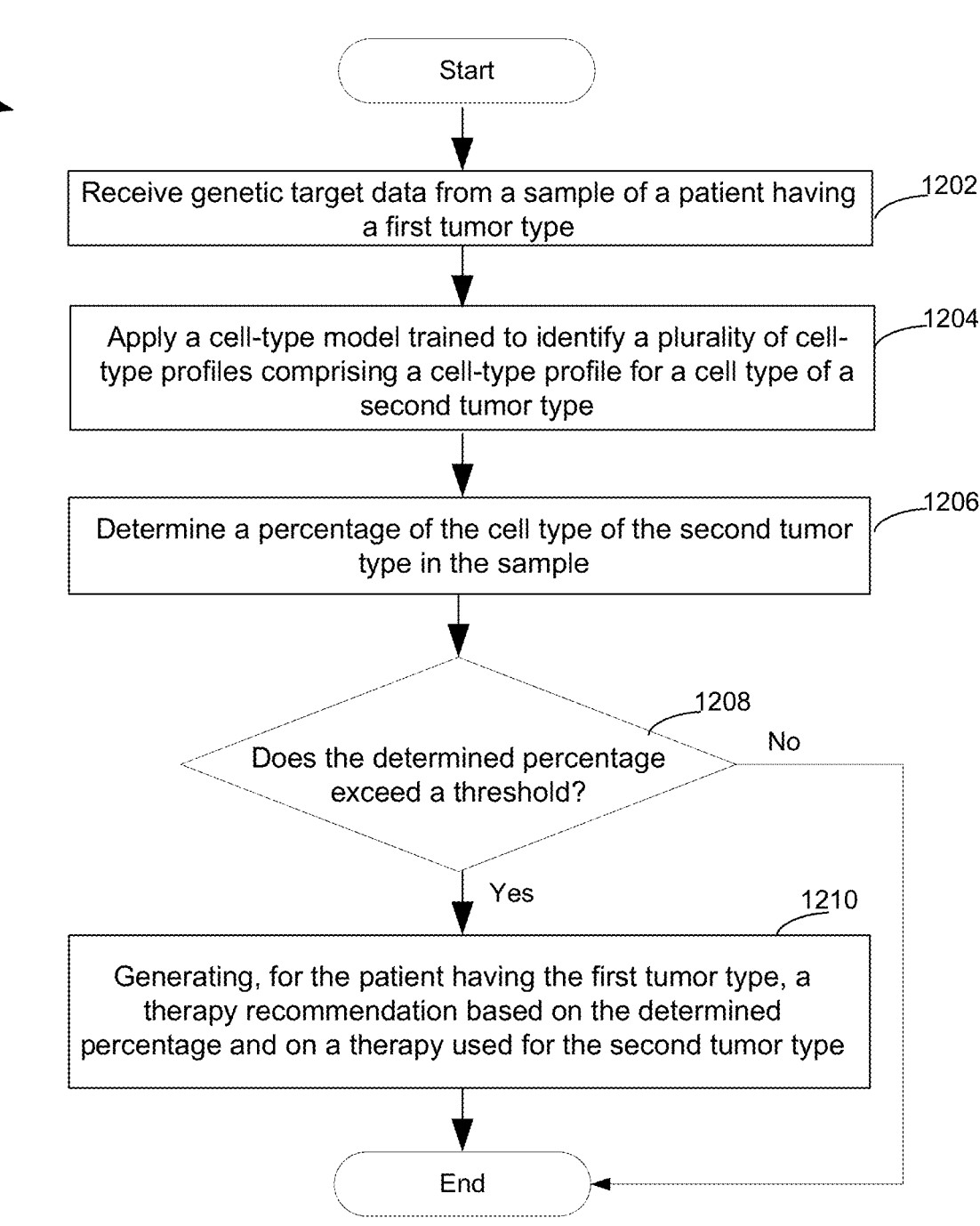
FIG. 12 is a flow chart illustrating a process of generating a therapy recommendation for a patient, in accordance with some embodiments of the present disclosure.

FIG. 12 illustrates an example of an embodiment of a process 1200 of generating a treatment recommendation using the approaches in accordance with various embodiments of the present disclosure. At block 1202 of FIG. 12, the process may receive genetic target data from a sample of a patient having a first tumor type, e.g., a breast tumor. The genetic target data may be, e.g., a test expression set. At block 1204, a cell-type model (e.g., the first and/or second optimization model described above in connection with FIG. 8), trained to identify a plurality of cell-type profiles comprising a cell-type profile for a cell type of a second tumor type, may be applied to the genetic target data received from the patient having the first tumor type.

The processing at block 1204 may be performed in accordance with any embodiments of the present disclosure, for example, using method 1000 (FIG. 10). The second tumor type can be a tumor different from the first tumor type and it can be, in an example, a prostate tumor. As discussed above, optimization models can be generated in accordance with embodiments of the present disclosure for any suitable tissue cell type. In some embodiments, the cell-type model may be selected such that the model is not trained to identify one or more (or all) cell types that may be present in the first tumor type but that it is trained to identify at least one cell type of the second tumor type. For example, in embodiments in which the first tumor type is a breast tumor and the second tumor type is a prostate tumor (though these tumors are discussed by way of example only), the model can be used to identify at least one cell type in the breast tumor that is typically present in the prostate tumor and may not have been previously identified in the breast tumor.

Next, at block 1206, as a result of the application of the plurality of cell-type profiles to the genetic target data received from the patient having the first tumor type, percentage of the cell type of the second tumor type in the sample may be determined. The cell type that can be present in different cancer tissues (e.g., in breast and prostate) may be referred to as a sub-lineage cell type. In some embodiments, shape and mean parameters of a gamma distributed can be estimated for each gene of the sub-lineage cell type.

At decision block 1208, it may be determined whether the determined percentage exceeds a certain threshold. In this way, it may be determined whether and to which degree the first tumor type of the patient includes a more cell type (or more than one cell types) that can also be found in a prostate tumor cell type. If the processing at block 1208 determines that the percentage determined at block 1206 exceeds the threshold, the process 1200 may generate, for the patient having the first tumor type, a therapy recommendation based on the determined percentage and on a therapy used for the second tumor type. For example, for the patient with breast cancer, determined to have a certain percentage of a cell type also found in a prostate cancer, the method 1200 may generate a therapy recommendation based on a therapy that is typically used for the prostate cancer treatment and may otherwise not be used for the treatment of breast cancer. In this way, a diagnosis and treatment recommendation based on cell types, in accordance with the present disclosure, may allow developing more precise and more personalized treatments that may otherwise not be apparent when cell types are not considered for a tissue type.

As shown in FIG. 12, after the therapy recommendation is generated at block 1210, which can be done in any suitable format (e.g., displayed on a user interface of a computing device or otherwise provided to a user), the process 1200 may end. As also shown in FIG. 12, if the determined percentage does not exceed the threshold (e.g., the first tumor type does not include, or includes a very small amount of cells similar to those found in the second tumor type), the process 1200 may also end.

In some embodiments, the described techniques may be used to model patient similarity by exchanging tumor tissue profiles percentages from one patient (e.g., patient A) to another patient (e.g., patient B), and comparing the change in likelihood between them. The difference between these patients may be visualized, e.g., as a distance metric to perform a radial plot graph of patient tumor similarity.

In some embodiments, the described technique may also be used for monitoring a progress of treatment. For example, it may be determined whether or not a tumor tissue sample from a patient undergoing a treatment has a certain cell type which may be indicative of a tumor malignancy, for example. Thus, if the cell type associated with a tumor malignancy is not found in the tumor tissue sample, it may be determined that the treatment has been effective in tumor reduction or prevention.

In some embodiments, techniques described herein may be used to predict a percentage of tumor present in the sample, percentages of tissue types present, type of tumor present, or the RNA expression of only the tumor. In some embodiments, a model in accordance with the present disclosure may be applied to a new tumor to compare to another type of tumor and to find similarities between other tumor types, identify a match to the other tumor type, and/or recommend a treatment that is effective against the other tumor type to treat the new tumor. In some embodiments, the techniques involve generating a sum of parts, where each part percentage is estimated using a model, wherein each part is individually balanced according to the mean and shape of a distribution model and balanced with each other gene according to the mean and shape of the distribution model, until the best fit for present cell types and their percentages are found.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "comprising," or any variation thereof, when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the terms "subject" or "patient" refers to any living or non-living human (e.g., a male human, female human, fetus, pregnant female, child, or the like). In some embodiments, a subject is a male or female of any stage (e.g., a man, a woman or a child).

As used herein the term "cancer," "cancerous tissue," or "tumor" refers to an abnormal mass of tissue in which the growth of the mass surpasses and is not coordinated with the growth of normal tissue. In the case of hematological cancers, this includes a volume of blood or other bodily fluid containing cancerous cells. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" or "somatic biopsy" refers to a biological sample obtained or derived from a tumor of a subject, as described herein.

Several aspects are described above with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

REFERENCES CITED

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of training a model for determining a cancer composition of a subject, the method comprising:
   at a computer system having one or more processors and memory storing one or more programs for execution by the one or more processors:
   obtaining, in electronic form, a set of relative RNA abundance values comprising, for each respective training subject in a plurality of training subjects, for each respective genetic target in a plurality of genetic targets, a corresponding relative RNA abundance value for the respective genetic target from bulk-cell RNA sequencing of one or more corresponding biological samples obtained from a corresponding tumor specimen of the respective training subject, wherein the plurality of training subjects is more than 100 training subjects and wherein no single-cell RNA-sequencing data or cell-type-specific expression profiles are provided to the computer system;

obtaining, in electronic form, a set of observed expression distribution parameters comprising, for each respective genetic target in the plurality of genetic targets, a corresponding observed shape parameter and a corresponding observed mean parameter by fitting a corresponding statistical distribution to a corresponding subset of the set of relative RNA abundance values comprising, for each respective training subject in the plurality of training subjects, the corresponding relative mRNA abundance value for the respective genetic target;

obtaining, in electronic form, a set of cell proportions comprising, for each respective training subject in the plurality of training subjects, for each respective cell type in a plurality of cell types, a corresponding proportion of the respective cell type in the one or more corresponding biological samples;

refining a first optimization model to correlate RNA abundance values for the plurality of genetic targets with proportions of the plurality of cell types, subject to a first plurality of constraints, the first plurality of constraints including:

(i) the corresponding observed shape parameter for each respective genetic target in the plurality of genetic targets, (ii) the set of cell proportions, and (iii) the set of relative RNA abundance values, thereby generating, for each respective cell type in the plurality of cell types, a corresponding cell type RNA expression profile.

2. The method of claim 1, wherein the first plurality of genetic targets comprises 10,000 genes.

3. The method of claim 1, wherein each genetic target in the plurality of genetic targets is a different RNA species for a corresponding gene in a plurality of genes.

4. The method of claim 1, wherein, for a respective subject in the plurality of subjects, the one or more corresponding biological samples are one or more pathology tissue slides.

5. The method of claim 4, wherein the one or more pathology tissue slides obtained from a respective subject in the plurality of subjects comprises between 5 and 20 pathology tissue slides.

6. The method of claim 1, wherein the corresponding relative RNA abundance value for the respective genetic target is a measure of central tendency of the relative abundance of RNA for the respective genetic target obtained based at least in part on the RNA sequencing of the one or more corresponding biological samples obtained from the tumor specimen of the respective subject.

7. The method of claim 1, wherein the plurality of cell types comprises one or more cancer cell types, one or more stromal cell types, one or more epithelial cell types, and one or more lymphocytic cell types.

8. The method of claim 1, wherein respective cell type in the plurality of cell types, the corresponding cell type RNA expression profile comprises, for each respective genetic target in the plurality of genetic targets, a corresponding set of fitted expression distribution parameters defining a distribution of relative abundance of the respective genetic target in the respective cell type.

9. The method of claim 1, wherein the plurality of genetic targets comprises at least 100 genes selected from the group consisting of ABCB1, ABCC3, ABL1, ABL2, ACTA2, ACVR1B, AJUBA, AKT1, AKT2, AKT3, ALK, AMER2, APC, APOB, AR, ARAF, ARHGAP26, ARHGAP35, ARID1A, ARID1B, ARID2, ARID5B, ASNS, ASXL1, AT1C, ATM, ATP7B, ATR, ATRX, AURKA, AURKB, AXIN1, AXIN2, AXL, B2M, BAP1, BARD1, BCL2, BCL2L1, BCL2L11, BCL6, BCL7A, BCL10, BCL11B, BCLAF1, BCOR, BCORL1, BCR, BIRC3, BLM, BMPR1A, BRAF, BRCA1, BRCA2, BRD4, BRIP1, BTG1, BTK, BUB1B, C3orf70, C8orf34, C10orf54, C10orf30, C10orf6, CALR, CARD11, CASP8, CASR, CBFB, CBL, CBLB, CBLC, CBR3, CBX6, CCND1, CCND2, CCND3, CCNE1, CD19, CD22, CD40, CD70, CD79A, CD79B, CD274, CDC73, CDH1, CDK4, CDK6, CDK8, CDK12, CDKN1A, CDKN1B, CDKN1C, CDKN2A, CDKN2B, CDKN2C, CEBPA, CEP57, CFTR, CHD2, CHD4, CHEK1, CHEK2, CIC, CIITA, CKS1B, CREBBP, CRKL, CRLF2, CSF1R, CSF3R, CTC1, CTCF, CTLA4, CTNNA1, CTNNB1, CTRC, CUX1, CXCR4, CYLD, CYP1B1, CYP2D6, CYP3A5, DAXX, DDB2, DDR2, DDX3X, DICER1, DIRC2, DIS3, DIS3L2, DKC1, DNM2, DNMT3A, DOT1L, DPYD, DYNC2H1, EBF1, ECT2L, EGF, EGFR, EGLN1, ELF3, ENG, EP300, EPCAM, EPHA2, EPHA7, EPHB1, EPHB2, EPOR, ERBB2, ERBB3, ERBB4, ERCC1, ERCC2, ERCC3, ERCC4, ERCC5, ERCC6, ERG, ERRFI1, ESR1, ETS1, ETS2, ETV1, ETV4, ETV5, ETV6, EWSR1, EZH2, FAM46C, FAM175A, FANCA, FANCB, FANCC, FANCD2, FANCE, FANCF, FANCG, FANCI, FANCL, FANCM, FAS, FAT1, FBXO11, FBXW7, FCGR2B, FCGR3A, FDPS, FGF1, FGF2, FGF3, FGF4, FGF5, FGF6, FGF7, FGF8, FGF9, FGF10, FGF14, FGF23, FGFR1, FGFR2, FGFR3, FGFR4, FH, FHIT, FLCN, FLG, FLT1, FLT3, FLT4, FNTB, FOXA1, FOXL2, FOXO1, FOXO3, FOXP1, FOXQ1, FRS2, FUBP1, G6PD, GALNT1, GATA1, GATA2, GATA3, GATA4, GATA6, GENT, GLI1, GNA11, GNA13, GNAQ, GNAS, GPC3, GPS2, GREM1, GRIN2A, GRM3, GSTP1, H3F3A, H19, HAS3, HAVCR2, HDAC1, HDAC2, HDAC4, HGF, HIF1A, HIST1H1C, HIST1H2AC, HIST1H3B, HLA-A, HLA-B, HLA-C, HLA-DMA, HLA-DMB, HLA-DOA, HLA-DOB, HLA-DPA1, HLA-DPB1, HLA-DPB2, HLA-DQA1, HLA-DQA2, HLA-DQB1, HLA-DQB2, HLA-DRA, HLA-DRB1, HLA-DRB5, HLA-DRB6, HNF1A, HNF4B, HOXB7, HRAS, HSP90AA1, HSPH1, IDH1, IDH2, IFIT2, IFIT5, IFNAR1, IFNAR2, IFNGR1, IFNGR2, IFNL3, IKBKE, IKZF4, IL2RA, IL6R, IL7R, IL10RA, IL15, ING1, INPP4B, IRF1, IRF2, IRF4, IRS2, ITPKB, JAK1, JAK2, JAK3, JUN, KAT6A, KDM5A, KDM5C, KDM6A, KDR, KEAP1, KEL, KIF1B, KIT, KLHL6, KLLN, KMT2A, KMT2B, KMT2C, KMT2D, KRAS, LAG3, LRP1B, LYN, LZTR1, MAD2L2, MAF, MAFB, MALT1, MAP2K1, MAP2K2, MAP2K4, MAP3K1, MAP3K13, MAPK1, MAX, MCL1, MDM2, MDM4, MED12, MEF2B, MENI, MET, MGMT, MIB1, MITF, MKI67, MLH1, MLH3, MLLT3, MPI, MRE11, MS4A1, MSH2, MSH3, MSH6, MTAP, MTHFR, MTOR, MTRR, MUTYH, MYB, MYC, MYCL, MYCN, MYD88, MYH11, NBN, NCOR1, NCOR2, NF1, NF2, NFE2L2, NFKBIA, NHP2, NKX2-1, NOP10, NOTCH1, NOTCH2, NOTCH3, NPM1, NQO1, NRAS, NRG1, NSD1, NTHL1, NTRK1, NTRK2, NTRK3, NUDT15, NUP98, P2RY8, PAK1, PALB2, PALLD, PARK2, PAX3, PAX5, PAX7, PAX8, PBRM1, PCBP1, PDCD1, PDCD1LG2, PDGFRB, PDG- FRA, PDK1, PDPKI, PHF6, PHOX2B, PIAS4, PIK3C2B, PIK3CA, PIK3CB, PIK3CD, PIK3CG, PIK3R1, PIK3R2, PIM1, PLCG2, PML, PMS1, PMS2, POLD1, POLE, POLH, POT1, POU2AF1, PPPIR1A, PPP2R1A, PPP2R2A, PPP6C, PRCC, PRDM1, PREX2, PRKAR1A, PRSS1, PRSS2, PTCH1, PTCH2, PTEN, PTPN11, PTPN13, PTPN22, PTPRD, RAC1, RAD21, RAD50, RAD51, RAD51B, RAD51C, RAD51D, RAD54L, RAF1, RANBP2, RARA, RASA1, RB1, RBM10, RECQL4, RET, RHOA, RICTOR, RINT1, RIT1, RNF43, RNF139, ROS1, RPL5, RPS6KA3, RPS15, RPTOR, RSF1, RUNX1, RXRA, SCG5, SDHA, SDHAF2, SDHB, SDHC, SDHD, SEC23B, SEMA3A, SETBP1, SETD2, SF3B1, SGK1, SH2B3, SLC26A9, SLC47A1, SLIT2, SLX4, SMAD2, SMAD3, SMAD4, SMARCA2, SMARCA4, SMARCB1, SMARCD1, SMC1A, SMC3, SMO, SOCS1, SOX2, SOX9, SOX10, SPEN, SPINK1, SPOP, SPRED1, SRC, SRSF2, STAG2, STAT3, STAT4, STAT5B, STAT6, STK11, SUFU, SUZ12, SYK, TAF1, TANC1, TAP1, TAP2, TBC1D32, TBL1XR1, TBX3, TCF3, TCF7L2, TCL1A, TERT, TET2, TGFBR1, TGFBR2, TIG1T, TMEM127, TMEM173, TMPRSS2, TNF, TNFAIP3, TNFRSF13B, TNFRSF14, TNFRSF17, TNFRSF1A, TNFRSF1B, TOP1, TOP2A, TP53, TP63, TPM1, TPMT, TRAF3, TSC1, TSC2, TSHR, TUSC3, TYMS, U2AF1, UBE2T, UGT1A1, UGT1A6, UMPS, VEGFA, VHL, WEE1, WHSC1, WRN, WT1, XPA, XPC, XPO1, XRCC1, XRCC2, XRCC3, YEATS4, ZFHX3, ZNF217, ZNF471, ZNF662, ZNF750, ZNRF3, and ZRSR2.

10. The method of claim 1, wherein, for each respective subject in the plurality of subjects, the corresponding tumor specimen from the respective subject is a tumor from a same origin.

11. The method of claim 1, wherein the refining uses k-fold cross validation of the plurality of subjects, subject to the first plurality of constraints.

12. The method of claim 1, wherein, for each respective genetic target in the plurality of genetic targets, the corresponding statistical distribution is a gamma distribution defined by the corresponding first shape parameter and a measure of central tendency for the subset of the set of relative RNA abundance values.

13. The method of claim 1, wherein, for a respective training subject in the plurality of training subjects, the corresponding proportion of each respective cell type in the plurality of cell types is derived from a pathology report for the corresponding subject.

14. The method of claim 1, further comprising:
obtaining, in electronic form, a test expression set that comprises, for each respective genetic target in the first plurality of genetic targets, a corresponding measure of central tendency of an abundance of the respective genetic target, based at least in part on RNA sequencing of one or more respective biological samples obtained from a tumor specimen of a test subject;
obtaining, in electronic form, a test proportion set that comprises, for each respective cell type in the first plurality of cell types, a corresponding estimate of the corresponding proportion of the respective cell type in the one or more respective biological samples; and
refining the corresponding estimate of the corresponding proportion of each respective cell type in the first plurality of cell types using a second optimization model subject to a second plurality of constraints, the second plurality of constraints including:
(i) the test expression set,
(ii) the test proportion set, and (iii) the corresponding cell type RNA expression profile for each respective cell type in the plurality of cell types, thereby identifying proportion of each calculated cell type in the plurality of calculated cell types in the tumor specimen.

15. The method of claim 1, wherein refining the first optimization model comprises:
(A) defining a set of calculated cell proportions comprising, for each respective training subject in the plurality of training subjects, for each respective cell type in the plurality of cell types, a corresponding calculated cell proportion bounded by the corresponding proportion of the respective cell type;
(B) refining a set of fitted expression distribution parameters comprising, for each respective genetic target in the plurality of genetic targets, for each respective cell type in the plurality of cell types, a corresponding fitted shape parameter and a corresponding fitted mean parameter that collectively define a cell type-specific statistical distribution of abundance of the respective genetic target in the respective cell type using at least (i) the set of cell proportions, (ii) the corresponding observed shape parameter for each respective genetic target in the first plurality of genetic targets, (iii) the set of relative RNA abundance values, and (iv) the set of calculated cell proportions; and
(C) refining the set of calculated cell proportions using at least (i) the set of fitted expression distribution parameters, (ii) the corresponding observed shape parameter for each respective genetic target in the first plurality of genetic targets, (iii) the set of relative RNA abundance values, and (iv) the set of cell proportions.

16. The method of claim 15, wherein the refining (B) is performed on a genetic target by genetic target and subject by subject basis.

17. The method of claim 15, wherein the plurality of cell types are cancer cell types and the set of cell proportions further comprises, for each respective training subject in the plurality of training subjects, a corresponding proportion for a second set of cell types that comprises one or more stromal cell types, a third set of cell types that comprises one or more epithelial cell types, and a fourth set of cell types that comprises one or more lymphocytic cell types, and the method further comprises obtaining, independent of the plurality of training subjects, for each respective cell type in the second, third, and fourth set of cell types, a corresponding cell type RNA expression profile, thereby obtaining a plurality of reference cell type RNA expression profiles, and wherein the refining (B) and (C) further uses the plurality of reference cell type RNA expression profiles.

18. The method of claim 15, wherein for each respective genetic target in the plurality of genetic targets, the corresponding observed shape parameter and the corresponding observed mean parameter define a corresponding gamma distribution of the expression of the respective genetic target across the plurality of training subjects, and for each respective genetic target in the plurality of genetic targets, for each respective cell type in the plurality of cell types, the corresponding cell type-specific statistical distribution is a gamma distribution defined by the corresponding fitted shape parameter and the corresponding fitted mean parameter.

19. The method of claim 15, wherein the refining (B) comprises:

(B.1) refining, for each respective genetic target in the plurality of genetic targets, for each respective cell type in the plurality of cell types, the corresponding fitted mean parameter, while holding the corresponding fitted shape parameter fixed, using at least (i) the set of cell proportions, (ii) the corresponding observed shape parameter for each respective genetic target in the plurality of genetic targets, (iii) the set of calculated cell proportions, and (iv) the corresponding fitted shape parameter; and (B.2) refining, for each respective genetic target in the plurality of genetic targets, for each respective cell type in the plurality of cell types, the corresponding fitted shape parameter, while holding the corresponding fitted mean parameter fixed, using at least (i) the set of cell proportions, (ii) the corresponding observed shape parameter for each respective genetic target in the plurality of genetic targets, (iii) the set of calculated cell proportions, and (iv) the corresponding fitted mean parameter.

20. The method of claim 19, wherein the refining (B.1) and the refining (B.2) is iteratively repeated until a second convergence criterion is satisfied, and wherein the second convergence criterion is optionally evaluated in accordance with a second gradient descent algorithm or a second gradient ascent algorithm.

21. The method of claim 1, wherein the first plurality of genetic targets are different human RNA transcripts comprising a plurality of RNA transcripts for at least one gene.

22. The method of claim 1, wherein, for each respective genetic target in the plurality of genetic targets, the statistical distribution is a gamma distribution defined by the corresponding shape parameter and a corresponding measure of central tendency of the relative RNA abundance values for the respective genetic target in the set in relative RNA abundance values.

23. The method of claim 1, wherein the corresponding proportion of one or more sets of cell types in a plurality of sets of cell types for a respective subject is obtained from a pathologist or by flow cytometry.

24. The method of claim 1, wherein the plurality of cell types comprises a tumor cell type and a healthy tissue cell type.

25. A computer system for training a model for determining a cancer composition of a subject, the computer system comprising:

at least one processor; and a memory, the memory storing at least one program for execution by the at least one processor, the at least one program comprising instructions for:

obtaining, in electronic form, a set of relative RNA abundance values comprising, for each respective training subject in a plurality of training subjects, for each respective genetic target in a plurality of genetic targets, a corresponding relative RNA abundance value for the respective genetic target from bulk-cell RNA sequencing of one or more corresponding biological samples obtained from a corresponding tumor specimen of the respective training subject, wherein the plurality of training subjects is more than 100 training subjects and wherein no single-cell RNA-sequencing data or cell-type-specific expression profiles are provided to the computer system;

obtaining, in electronic form, a set of observed expression distribution parameters comprising, for each respective genetic target in the plurality of genetic targets, a corresponding observed shape parameter and a corresponding observed mean parameter by fitting a corresponding statistical distribution to a corresponding subset of the set of relative RNA abundance values comprising, for each respective training subject in the plurality of training subjects, the corresponding relative mRNA abundance value for the respective genetic target;

obtaining, in electronic form, a set of cell proportions comprising, for each respective training subject in the plurality of training subjects, for each respective cell type in a plurality of cell types, a corresponding proportion of the respective cell type in the one or more corresponding biological samples;

refining a first optimization model to correlate RNA abundance values for the plurality of genetic targets with proportions of the plurality of cell types, subject to a first plurality of constraints, the first plurality of constraints including:

(i) the corresponding observed shape parameter for each respective genetic target in the plurality of genetic targets, (ii) the set of cell proportions, and (iii) the set of relative RNA abundance values, thereby generating, for each respective cell type in the plurality of cell types, a corresponding cell type RNA expression profile.

26. A non-transitory computer-readable storage medium having stored thereon program code instructions that, when executed by a processor, cause the processor to perform a method for determining a cancer composition of a subject, the method comprising:

obtaining, in electronic form, a set of relative RNA abundance values comprising, for each respective training subject in a plurality of training subjects, for each respective genetic target in a plurality of genetic targets, a corresponding relative RNA abundance value for the respective genetic target from bulk-cell RNA sequencing of one or more corresponding biological samples obtained from a corresponding tumor specimen of the respective training subject, wherein the plurality of training subjects is more than 100 training subjects and wherein no single-cell RNA-sequencing data or cell-type-specific expression profiles are provided to the computer system;

obtaining, in electronic form, a set of observed expression distribution parameters comprising, for each respective genetic target in the plurality of genetic targets, a corresponding observed shape parameter and a corresponding observed mean parameter by fitting a corresponding statistical distribution to a corresponding subset of the set of relative RNA abundance values comprising, for each respective training subject in the plurality of training subjects, the corresponding relative mRNA abundance value for the respective genetic target;

obtaining, in electronic form, a set of cell proportions comprising, for each respective training subject in the plurality of training subjects, for each respective cell type in a plurality of cell types, a corresponding proportion of the respective cell type in the one or more corresponding biological samples;

refining a first optimization model to correlate RNA abundance values for the plurality of genetic targets with proportions of the plurality of cell types, subject to a first plurality of constraints, the first plurality of constraints including:

(i) the corresponding observed shape parameter for each respective genetic target in the plurality of genetic targets, (ii) the set of cell proportions, and (iii) the set of relative RNA abundance values, thereby generating, for each respective cell type in the plurality of cell types, a corresponding cell type RNA expression profile.

\* \* \* \* \*